US008022095B2

(12) United States Patent
Plachetka

(10) Patent No.: US 8,022,095 B2
(45) Date of Patent: *Sep. 20, 2011

(54) METHODS OF TREATING HEADACHES USING 5-HT AGONISTS IN COMBINATION WITH LONG-ACTING NSAIDS

(75) Inventor: John R. Plachetka, Chapel Hill, NC (US)

(73) Assignee: Pozen, Inc., Chapel Hill, NC (US)

( * ) Notice: Subject to any disclaimer, the term of this patent is extended or adjusted under 35 U.S.C. 154(b) by 799 days.

This patent is subject to a terminal disclaimer.

(21) Appl. No.: 10/414,493

(22) Filed: Apr. 16, 2003

(65) Prior Publication Data
US 2003/0232876 A1 Dec. 18, 2003

Related U.S. Application Data

(60) Continuation-in-part of application No. 09/559,753, filed on Apr. 27, 2000, now Pat. No. 6,586,458, which is a continuation-in-part of application No. 09/151,912, filed on Sep. 11, 1998, now Pat. No. 6,060,499, and a continuation-in-part of application No. 09/252,278, filed on Feb. 19, 1999, now abandoned, which is a division of application No. 08/907,826, filed on Aug. 14, 1997, now Pat. No. 5,872,145.

(60) Provisional application No. 60/024,129, filed on Aug. 16, 1996.

(51) Int. Cl.
A61K 31/405 (2006.01)
C07C 49/00 (2006.01)
C07C 49/215 (2006.01)

(52) U.S. Cl. ........ 514/415; 514/461; 424/464; 568/328; 568/331

(58) Field of Classification Search .................. 424/464; 514/415, 461, 449, 473
See application file for complete search history.

(56) References Cited

U.S. PATENT DOCUMENTS

| 701,438 | A | 6/1902 | Whyte | |
|---|---|---|---|---|
| 2,951,792 | A | 9/1960 | Swintosky | |
| 3,048,526 | A | 8/1962 | Boswell | |
| 3,317,394 | A | 5/1967 | Ostholm | |
| 3,358,687 | A | 12/1967 | Miley et al. | |
| 4,024,279 | A | 5/1977 | Zor et al. | 424/319 |
| 4,786,500 | A | 11/1988 | Wong | |
| 4,814,181 | A | 3/1989 | Jordan et al. | |
| 4,816,470 | A | 3/1989 | Dowle et al. | 514/415 |
| 4,844,907 | A | 7/1989 | Elger et al. | |
| 4,946,685 | A | 8/1990 | Edgren et al. | |
| 5,004,613 | A | 4/1991 | Radebaugh et al. | |
| 5,037,845 | A | 8/1991 | Oxford | |
| 5,041,430 | A * | 8/1991 | Addicks et al. | 514/161 |
| 5,307,845 | A | 5/1994 | Vanrobaeys et al. | 139/1 R |
| 5,307,953 | A | 5/1994 | Regan | 222/82 |
| 5,360,925 | A | 11/1994 | Chabrier de Lassauniere et al. | 560/169 |
| 5,387,604 | A | 2/1995 | McDonald et al. | 514/456 |
| 5,425,950 | A | 6/1995 | Dandiker et al. | 424/480 |
| 5,430,021 | A * | 7/1995 | Rudnic et al. | 514/14 |
| 5,474,995 | A | 12/1995 | Ducharme et al. | 514/241 |
| 5,480,650 | A | 1/1996 | Marchi et al. | 424/464 |
| 5,514,168 | A | 5/1996 | Friedman | 607/89 |
| 5,554,639 | A | 9/1996 | Craig et al. | 514/415 |
| 5,605,917 | A | 2/1997 | Ogletree | 514/365 |
| 5,607,960 | A | 3/1997 | Wythes | 514/414 |
| 5,618,816 | A | 4/1997 | Crenshaw et al. | 514/253 |
| 5,637,320 | A | 6/1997 | Bourke et al. | 424/489 |
| 5,698,571 | A | 12/1997 | Audia et al. | 514/323 |
| 5,705,520 | A | 1/1998 | Craig et al. | 514/415 |
| 5,738,874 | A | 4/1998 | Conte et al. | |
| 5,807,571 | A | 9/1998 | List | 424/449 |
| 5,872,145 | A | 2/1999 | Plachetka | 514/415 |
| 5,914,129 | A * | 6/1999 | Mauskop | 424/464 |
| 5,942,503 | A | 8/1999 | Jung et al. | 514/214 |
| 6,039,974 | A | 3/2000 | MacLaren et al. | |
| 6,060,499 | A | 5/2000 | Plachetka | 514/415 |
| 6,077,539 | A | 6/2000 | Plachetka et al. | |
| 6,183,779 | B1 | 2/2001 | Ouali et al. | |
| 6,228,398 | B1 | 5/2001 | Devane et al. | |
| 6,245,802 | B1 | 6/2001 | Iyengar et al. | 514/438 |
| 6,365,184 | B1 | 4/2002 | Depui et al. | 424/469 |
| 6,368,627 | B1 | 4/2002 | Phillips et al. | 424/480 |
| 6,372,255 | B1 | 4/2002 | Saslawski et al. | |
| 6,384,034 | B2 | 5/2002 | Simitchieva et al. | 514/252 |
| 6,387,410 | B1 | 5/2002 | Woolfe et al. | 424/489 |
| 6,586,458 | B1 * | 7/2003 | Plachetka | 514/415 |

(Continued)

FOREIGN PATENT DOCUMENTS

AU 711741 3/1998

(Continued)

OTHER PUBLICATIONS

News, FDA http://www.fda.gov/bbs/topics/NEWS/NEW00456.html Jan. 1994 p. 1.*
Certified Translation of AG2 below.
Andersson, et al., "Double-Blind Study of Naproxen vs Placebo in the Treatment of Acute Migraine Attacks," *Cephalalgia* 9:29-32 (1989).
Baumel, "Migraine: A Pharmacologic Review with Newer Options and Delivery Modalities," *Neurology* 44:S13-S17 (1994).
Bolten, "Scientific Rationale for Specific Inhibition of COX-2," *J. Rheumatol.* 25:2-7 (1998).
Boureau, et al., "Comparison of Subcutaneous Sumatriptan with Usual Acute Treatments for Migraine," *Eur. Neurol.* 35:264-269 (1995).
Bousser, et al., "Combined Low-Dose Acetylsalicylic Acid and Dihydroergotamine in Migraine Prophylaxis," *Cephalalgia* 8:187-102 (1988).

(Continued)

Primary Examiner — Frederick Krass
Assistant Examiner — Lezah W Roberts
(74) Attorney, Agent, or Firm — Meyertons, Hood, Kivlin, Kowert & Goetzel, P.C.; Eric B. Meyertons

(57) ABSTRACT

The invention is directed to methods and compositions that can be used in the treatment of headaches. In particular, methods and compositions are described involving the combination of a long-acting NSAID and a 5-HT$_{1B}$/$1_D$ agonist.

6 Claims, No Drawings

U.S. PATENT DOCUMENTS

| | | | |
|---|---|---|---|
| 6,635,281 | B2 | 10/2003 | Wong et al. |
| 6,797,283 | B1 | 9/2004 | Edgren et al. |
| 6,863,901 | B2 | 3/2005 | Hirsh et al. |
| 2002/0016348 | A1 | 2/2002 | Simitchieva et al. |
| 2002/0099059 | A1 | 7/2002 | Saper ............... 514/263.31 |
| 2003/0203027 | A1 | 10/2003 | Verreck et al. |
| 2003/0232876 | A1 | 12/2003 | Plachetka |
| 2004/0180089 | A1 | 9/2004 | Plachetka et al. ............ 424/472 |
| 2007/0184109 | A1 | 8/2007 | Floyd et al. |
| 2008/0287451 | A1 | 11/2008 | Cook et al. |
| 2009/0068262 | A1 | 3/2009 | Zalit et al. |
| 2009/0186086 | A1 | 7/2009 | Shankar et al. |
| 2009/0252791 | A1 | 10/2009 | Sreedharala et al. |

FOREIGN PATENT DOCUMENTS

| | | |
|---|---|---|
| CA | 2 260 943 | 2/1998 |
| CS | 277 525 | 2/1993 |
| DE | 195 42 281 | 5/1997 |
| EP | 0 117 164 | 8/1984 |
| EP | 0 397 314 | 7/1990 |
| EP | 0 447 727 | 9/1991 |
| EP | 0 656 776 B1 | 3/1996 |
| EP | 0 605 697 | 3/1999 |
| EP | 0605697 | 3/1999 |
| EP | 0 957 914 | 11/1999 |
| EP | 1 051 993 | 11/2000 |
| EP | 1 051 995 | 11/2000 |
| EP | 1 064 948 | 1/2001 |
| EP | 1 064 966 | 1/2001 |
| EP | 1 064 967 | 1/2001 |
| EP | 1 126 841 | 12/2004 |
| GB | 2 005 538 A | 4/1979 |
| GB | 2 113 546 A | 8/1983 |
| GB | 2 124 210 | 2/1984 |
| GB | 2 124 210 A | 2/1984 |
| GB | 2 135 884 | 9/1984 |
| GB | 2 162 522 | 2/1986 |
| JP | 8-208516 | 8/1996 |
| JP | 2000-336027 | 12/2000 |
| WO | WO 94/26270 | 11/1994 |
| WO | WO 95/01781 | 1/1995 |
| WO | WO 95/20946 | 8/1995 |
| WO | WO 97/38986 | 10/1997 |
| WO | WO 98/06392 | 2/1998 |
| WO | WO 98/15275 | 4/1998 |
| WO | WO 98/20870 | 5/1998 |
| WO | WO 99/45905 | 9/1999 |
| WO | WO 00/06161 | 2/2000 |
| WO | WO 00/25779 | 5/2000 |
| WO | WO 00/48583 | 8/2000 |

OTHER PUBLICATIONS

Bousser, et al., "Efficacy of Subcutaneous Sumatriptan in the Acute Treatment of Early-Morning Migraine: A Placebo-Controlled Trial," *J. Intern. Med.* 234:211-216 (1993).

Cady, et al., "Treatment of Acute Migraine with Subcutaneous Sumatriptan," *JAMA* 265:2831-2835 (1991).

Cady, et al., "Efficacy of Subcutaneous Sumatriptan in Repeated Episodes of Migraine," *Neurology* 43:1363-1368 (1993).

Capobianco, et al., "An Overview of the Diagnosis and Pharmacologic Treatment of Migraine," *Mayo Clin. Proc.* 71:1055-1066 (1996).

Centonze, et al., "Evaluation of the Efficacy of Oral Sumatriptan in the Management of Migraine Attacks. Clinical Results," *La Clinica Teraputica* 146:721-728 (1995).

Dahlöf, "How Does Sumatriptan Perform in Clinical Practice," *Cephalalgia* 15:21-28 (1995).

Dechant, et al., "Sumatriptan—A Review of Its Pharmacodynamic and Pharmacokinetic Properties, and Therapeutic Efficacy in the Acute Treatment of Migraine and Cluster Headache," *Drugs* 43:776-798 (1992).

Demarin, et al., "Pharmacotherapy of Migraine," *Acta Clin. Croat.* 34:81-89 (1995).

Donnelly, et al., "Review Article: COX-II Inhibitors—A New Generation of Safer NSAIDs?," *Aliment. Pharmacol. Ther.* 11:227-236 (1997).

Furlong, et al., "Prescribing Practices for the Management of Headache in Newfoundland and Labrador," *Headache* 36:542-546 (1996).

Furst, "Meloxicam: Selective COX-2 Inhibition in Clinical Practice," *Semin. Arthritis Rheum.* 26:21-27 (1997).

Grazzi, et al., "A Review of the Treatment of Primary Headaches. Part I: Migraine," *Intl. J. Neurol. Sci.* 16:577-586 (1995).

Griswold, et al., "Constitutive Cyclooxygenase (COX-1) and Inducible Cyclooxygenase (COX-2): Rationale for Selecive Inhibition and Progress to Date," *Med Res. Rev.* 16:181-206 (1996).

Haag, "Kombianalgetika in der Kopfschmerz-therapie," *Duetsche Apotheker Zeitung, De, Deutscher Apotheker Zeitung* 4:43-48 (1993) Stuttgart.

Hoernecke, et al., "Treatment of Migraine Attacks: Combination of Dihydroergotamine Tartrate and Paracetamol in Comparison with Individual Drugs and Placebo," *Medizinische Klinik* 88:642-648 (1993); Abstract from Medline Online, Database Accession No. NLM8295604.

Klapper, "The Pharmacologic Treatment of Acute Migraine Headaches," *J. Pain Symptom Manage.* 8:140-147 (1993).

Klapper, "Toward a Standard Drug Formulary for the Treatment of Headache," *Headache* 35:225-227 (1995).

Kumar, "Recent Advances in the Acute Management of Migraine and Cluster Headaches," *J. Gen. Internal Med.* 9:339-348 (1994).

Krymchantowski, et al., "Tolfenamic Acid Decreases Migraine Recurrence When Used with Sumatriptan," *Cephalalgia* 19:186-187 (1999).

Krymchantowski, et al., "Naproxen Sodium Decreases Migraine Recurrence When Used with Sumatriptan," *Cephalalgia* 19:357-358 (1999).

Lance, "Headache," *Ann. Neurol.* 10:1-10 (1981).

Lane, "Pain Management in Osteoarthritis: The Role of COX-2 Inhibitors," *J. Rheumatol.* 24:20-24 (1997).

Lipsky, et al., "Outcome of Specific COX-2 Inhibition in Rheumatoid Arthritis," *J. Rheumatol.* 24:9-14 (1997).

Mathew, "Cyclical Prophylactic Treatment of Menstrual Migraine Using Naproxen and Ergotamine," *Headache* 26:314 (1986).

Mathew, et al., "Advances in Migraine Drug Therapy," *Drug Therapy* 23:37-48 (1993).

Moskowitz, et al, "Neuroeffector Functions of Sensory Fibres: Implications for Headache Mechanisms and Drug Actions," *J. Neurol.* 238:S-18-S22 (1991).

Myllylä, et al., "Tolfenamic Acid Rapid Release Versus Sumatriptan in the Acute Treatment of Migraine: Comparable Effect in a Double-Blind, Randomized, Controlled, Parallel-Group Study," *Headache* 38:201-207 (1998).

Oral Sumatriptan Group, "Sumatriptan—An Oral Dose-Defining Study," *Eur. Neurol.* 31:300-305 (1991).

Parma, et al., "Il Trattamento dell'Emicrania: Uno Studio Nella Medicina Generale," *Ricerca & Pratica* 11:64-72 (1995) in Italian.

Translation of AK5 above: Parma, et al., "The Treatment of Migraine: A Study in General Medicine," *Ricerca & Pratica* 11:64-72 (1995).

Pavel, et al., "Formulation of Antimigraine Mixtures," *STN HCA* 8 (1994), Abstract XP-002078672.

Peroutka, "Beyond Monotherapy: Rational Polytherapy in Migraine," *Headache* 38:18-22 (1998).

Pfaffenrath, et al., "Efficacy and Safety of Sumatriptan Tablets (25 mg, 50 mg, and 100 mg) in the Acute Treatment of Migraine: Defining the Optimum Doses of Oral Sumatriptan," *Headache* 38:184-190 (1998).

Plosker, et al., "Sumatriptan: A Reappraisal of Its Pharmacology and Therapeutic Efficacy in the Acute Treatment of Migraine and Cluster Headache," *Drugs* 47:622-651 (1994).

Pradalier, et al., "La Migraine Cataméniale," *Contracept. Fertil. Sex.* 23:361-365 (1995) in French.

Translation of AP5 above: Pradalier, et al., "Menstrual Migraine," *Contracept Fertil. Sex.* 23:361-365 (1995).

Rac, et al., "Formulation of Antimigraine Mixtures," STN HCA, vol. 8 (1994), abstract—XP-002078672.

Saadah, "Abortive Migraine Therapy with Oral Naproxen Sodium Plus Metoclopramide Plus Ergotamine Tartrate with Caffeine," *Headache* 32:95-97 (1992).

Schuller, et al., "Recurrent Headaches: What Every Allergist Should Know," *Ann. Allergy Asthma Immunol.* 76:219-230 (1996).

Sharma, et al., "An Update on Eicosanoids and Inhibitors of Cyclooxygenase Enzyme Systems," *Indian J. Exper. Biol.* 35:1025-1031 (1997).
Sheftell, et al., "Subcutaneous Sumatriptan in a Clinical Setting: The First 100 Consecutive Patients with Acute Migraine in a Tertiary Care Center,"*Headache* 34:67-72 (1994).
Silberstein, "Treatment of the Migraine Attack," *Curr. Opn. Neurol.* 7:258-263 (1994).
Solomon, "Therapeutic Advances in Migraine," *J. Clin. Pharmacol.* 33:200-209 (1993).
Thomson, "A Study to Compare Oral Sumatriptan with Oral Aspirin plus Oral Metoclopramide in the Acute Treatment of Migraine," *Eur. Neurol.* 32:177-184 (1992).
Todd, et al., "Naproxen: A Reappraisal of Its Pharmacology, and Therapeutic Use in Rheumatic Diseases and Pain States," *Drugs* 40:91-137 (1990).
Tokola, et al., "Effects of Migraine Attack and Metoclopramide on the Absorption of Tolfenamic Acid," *Br. J. Clin. Pharmac.* 17:67-75 (1984).
Tokola, et al., "Tolfenamic Acid, Metroclopramide, Caffeine and their Combinations in the Treatment of Migraine Attacks," *Cephalalgia* 4:253-263 (1984).
Von Seggern, et al., "Cost Considerations in Headache Treatment Part 2: Acute Migraine Treatment," *Headache* 36:493-502 (1996).
Welch, "Drug Therapy of Migraine," *N. E. J. Med.* 329:1476-1483 (1993).
Wilkinson, et al., "Migraine Cluster Headache—their Management with Sumatriptan: A Critical Review of the Current Clinical Experience," *Cephalalgia* 15:337-357 (1995).
Wittig, "Renal Papillary Necrosis Following Emergency Department Treatment of Migraine," *J. Emer. Med.* 14:373-376 (1996).
Dialog Abstract of German patent document DE 195 42 281.
Abstracts of Talley, et al., O.D. Searle Celebrex Registry 169590-42-5, "Celebrex," SC58635, patents for migraine headache: 5,466,823 (Nov. 1995); 5,504,215 (Apr. 1996); 5,508,426 (Apr. 1996); 5,510,496 (Apr. 1996); 5,516,907 (May 1996); 5/521,207 (May 1996); 5,563,165 (Oct. 1996); 5,700,816 (Dec. 1997); 5,753,688 (May 1998); 5,760,068 (Jun. 1998); and 5,932,598 (Aug. 1999).
Cady, et al., "Recent Advances in Migraine Management,"*J. Family Practice* 36(1):85-91 (1993).
Prusinski, "Monotherapy or Polytherapy in Migraine", *Neuroepidemiology* 6:186-189 (1987).
English language abstract for WO 94/26270.
English language abstract for JP 8-208516.
Buzzi, et al., "Evidence for 5-HT1B/1D Receptors Mediating the Antimigraine Effect of Sumatriptan and Dihydroergotamine," *Cephalalgia* 11:165-168 (1991).
Sternfeld, et al., "The Chemical Evolution of N,N-Dimethyl-2 [5-(1,2,4-Triazol-4-YL)-1H-Indol-3-YL]Ethylamine (L-741,604) and Analogues: Potent and Selective Agonists for 5-HT$_{1D}$ Receptors," *Biorganic and Medicinal Chemistry Letters* 6(15):1825-1830 (1996).
Extract from *The Pharmacological Basis of Therapeutics*, Goodman & Gilman, 9$^{th}$ Ed.
*The Merck Index*, 12$^{th}$ Ed., 1996: THER-12-13.
*The Merck Index*, 13$^{th}$ Ed., 2001:1480.
*Physicians' Desk Reference*,® 50$^{th}$ Ed., 1996, Imitrex®:1106-1110.
*Physicians' Desk Reference*,® 50$^{th}$ Ed., 1996, Naproxen®:2110-2113.
Search results obtained from the "Integrity" and "Pharmaprojects" databases, following a query for "ALX-1323."
Test Report prepared by Opponent Almirall Prodesfarma SA.
Opposition papers filed by Opponent Almirall Prodesfarma SA.
Opposition papers filed by Opponent Merck & Co., Inc.
English language translation for CS 277 525.
Brandes, et al., "Superior Efficacy of Combination Therapy over Monotherapy: Results of a Fixed Single-Tablet Formulation of Sumatriptan RT Technology and Naproxen Sodium in the Acute Treatment of Migraine in the Traditional Treatment Paradigm," Abstract (accepted for presentation), 48$^{th}$ Annual Scientific Meeting of the American Headache Society, Jun. 22-26, Los Angeles, CA.

Brandes, et al. "Therapeutic Clinical Benefits of a New Single-Tablet Formulation of Sumatriptan Formulated with RT Technology™ and Naproxen Sodium," *Cephalalgia* 25:860 (2005).
Dahlöf, "Infrequent or Non-Response to Oral Sumatriptan Does Not Predict Response to Other Triptans—Review of Four Trials," *Cephalalgia* 26:98-106 (2005).
Ferrari, et al., "Triptans (serotonin, 5-HT$_{1B/1D}$ Agonists) in Migraine: Detailed Results and Methods of a Meta-Analysis of 53 Trials," *Cephalalgia* 22:633-658 (2002).
Fowler, et al., "The Effect of Anti-Prostaglandins and Anti-Histamines on the Tolerability Profile of Sumatriptan," *New Adv. Headache Res.* 4:318 (1994).
Fuseau, et al., "Effect of Encapsulation on Absorption of Sumatriptan Tablets: Data from Healthy Volunteers and Patients During a Migraine," *Clin. Therapeutics* 23:242-251 (2001).
Krymchantowski, et al., "Rizatriptan Versus Rizatriptan Plus Rofecoxib Versus Rizatriptan Plus Tolfenamic Acid in the Acute Treatment of Migraine," *BMC Neurology* 4:10 (2004).
Krymchantowski, "Naproxen Sodium Decreases Migraine Recurrence When Administered with Sumatriptan," *Arq Neuropsiquiatr* 58(2-B):428-430 (2000).
Krymchantowski, et al., "Rizatriptan Combined with Rofecoxib vs. Rizatriptan for the Acute Treatment of Migraine: An Open Label Pilot Study," *Cephalalgia* 22:309-312 (2002).
Louis, et al., "Crossover and Self-Controlled Designs in Clinical Research," *N. Engl. J. Med.* 310:24-31(1984).
Mandema, et al., "Therapeutic Benefit of Eletriptan Compared to Sumatriptan for the Acute Relief of Migraine Pain—Results of a Model-Based Meta-Analysis that Accounts for Encapsulation," *Cephalalgia* 25:715-725 (2005).
Silberstein, et al., "Superior Clinical Benefits of a New Single-Tablet Formulation of Sumatriptan Formulated with RT Technology and Naproxen Sodium," Abstract S35.001, 58$^{th}$ Annual Meeting of the American Academy of Neurology, presented Apr. 5, 2006, San Diego, CA.
Smith, et al., "Sumatriptan and Naproxen Sodium for the Acute Treatment of Migraine," *Headache* 45:983-991 (2005).
Spierings, "Eletriptan in Acute Migraine: A Double-Blind, Placebo-Controlled Comparison to Sumatriptan," *Neurology* 55:735-742 (2000).
Visser, et al., "Risk Factors for Headache Recurrence after Sumatriptan: A Study in 366 Migraine Patients," *Cephalalgia* 16:264-269 (1996).
Various Letters to the Editor, *Headache* 921-929 (Sep. 2003).
Extract from *The Pharmacological Basis of Therapeutics*, Goodman & Gilman, 9$^{th}$ Ed., pp. 231 and 491-498.
Response filed in European Oppositions of Merck and Almirall.
Comparison of Chemical Structures of Ergots and Triptans, *Modern Drug Discovery*, vol. 2 (1999).
Brandes, et al., "Sumatriptan-Naproxen for Acute Treatment of Migraine," *JAMA*, vol. 297, 1443-1454 (Apr. 2007).
Kumar, et al., "Headaches" *Medical Clinics of North America* 79(2):261-286 (Mar. 1995).
Solomon, "The Pharmacology of Medications Used in Treating Headache," *Seminars in Pediatric Neurology* 2(2):165-177 (Jun. 1995).
Tfelt-Hansen, "Sumatriptan for the Treatment of Migraine Attacks: A Review of Controlled Clinical Trials," *Cephalalgia* 13:238-244 (1993).
Blanco, et al., "Effect of Antiinflammatory Drugs on COX-1 and COX-2 Activity in Human Articular Chondrocytes," *J. Rheumatology* 26(6):1366-1373 (1999).
Feldman, et al., "Do Cyclooxygenase-2 Inhibitors Provide Benefits Similar to Those of Traditional Nonsteroidal Anti-Inflammatory Drugs, with Less Gastrointestinal Toxicity?" *Ann. Inter. Med.* 132(2):134-143 (Jan. 2000).
Insel, Paul A., "Analgesic-Antipyretic and Antiinflammatory Agents and Drugs Employed in the Treatment of Gout," Goodman & Gilman's *The Pharmacological Basis of Therapeutics* 9$^{th}$ ed. Chapter 27 pp. 617-657 (1995).
Tfelt-Hansen, et al., "Triptans in Migraine: A Comparative Review of Pharmacology, Pharmacokinetics and Efficacy," *Drugs* 60(6):1260-1287 (Dec. 2000).

Buzzi, et al., Evidence for 5-HT1B-1D Receptors mediating the antimigraine effect of sumatriptan and dihydroergotamine, *Cephalalgia* 11:165-168 (1991)—Biosis abstract.

Martelletti, et al., Upregulated expression of peripheral serotonergic receptors in migraine and cluster headache by sumatriptan, *Intern'l J. Pharmacol. Res.* 14:165-175 (1995)-Biosis abstract.

Schwarzberg, M., Application of metoclopramide specificity in migraine attacks therapy, *Headache* 34:439-441 (1994); Biosis abstract.

Silberstein, S., The pharmacology of ergotamine and dihydroergotamine, *Headache* 37:S15-S25(1997)—Biosis abstract.

Zgombick, et al., Pharmacological characterizations of recombinant human 5-HT-1Dalpha and 5-HT-1Dbeta receptor subtypes coupled to adenylate cyclase inhibition in clonal cell lines: apparent differences in drug intrinsic efficacies between human 5-HT-1Dalpha subtypes, *Naunyn-Schmiedeberg's Archives of Pharmacol.* 354:226-236 (1996)—Biosis abstract.

Raskin, *Neurology* 43 (suppl 3):S39-S42 (1993).

Imitrex labeling approved Jun. 1, pp. 1-24 (1992).

Original Complaint filed by Pozen Inc. in the US District Court for the Eastern District of Texas, Tyler Division, dated Nov. 14, 2008, and including copies of patents US 6,060,499; US 6,586,458; and US 7,332,183.

Answer and Counterclaims to Original Complaint filed by Par Pharmaceutical, Inc. in the US District Court for the Eastern District of Texas, Tyler Division, and dated Dec. 8, 2008.

Aulton, Michael E., ed. *"Pharmaceutics: The Science of Dosage Form Design,"* Churchill Livingstone pp. 304-321 (1988).

Balasny, et al., "Treatment of Childhood Migrane in a Hospital Based Neurology Clinic," *Children's Hospital Quarterly* 8(2):81-84 (1996).

Bandelin, F.J. "Compressed Tablets by Wet Granulation," *Pharmaceutical Dosage Forms: Tablets,* 1989:1:179-80 (Herman A. Lieberman et al., eds.).

Brandes J.L., "Global Trends in Migrane Care: Results from the MAZE Survey," *CNS Drugs* 16(Suppl. 1): 13-18, (2002).

Burtscher, et al., "Ibuprofen Versus Sumatriptan for High-Altitude Headache," *Lancet* 346:254-255 (Jul. 22, 1995).

Cady, R.R. "Diagnosis and Treatment of Migraine," *Headache* 1 (6):21-32 (1999).

Carstensen, Jens T., "Pharmaceutics of Solids and Solid Dosage Forms," John Wiley & Sons, pp. 63-87 (1977).

Dahlof, C. "Headache Reccurrence After Subcutaneous Sumatriptan and Early Treatment," *Lancet* 340:909 (Oct. 10, 1992).

Dahlof, C. "How to Assess Patient Preference of Migrane Treatments," *Cephalalgia* 19(Suppl.24):2-6 (1999).

Dahlof, C., "Would Any Acute Treatment for Migraine Demonstrate Recurrence?," *Cephalalgia* 17(Suppl.17):17-20 (1997).

Diamond, S., "Diagnosis and Treatment of Migraine," *Headache Quarterly, Current Treatment and Research* 4(1):8-14 (1993).

Diamond, S., "The Management of Migraine and Cluster Headaches," *Comprehensive Therapy* 21(9):492-98 (1995).

Diener, et al., "A Practical Guide to the Management and Prevention of Migraine," *Drugs* 56(5):811-824 (Nov. 1998).

Diener, et al., "Acute Management of Migraine: Triptans and Byond," *Curr. Opin. Neurol.* 12(3):261-267 (Jun. 1999).

Diener, et al., "Antimigraine Drugs," *J. Neurol.* 246:515-519 (1999).

Deleu, et al., "Symptomatic and Prophylactic Treatment of Migraine: A Critical Reappraisal," *Clin. Neurophama* 21(5):267-279 (1998).

Dodick, D.W., "Acute and Prophylatic Management of Migraine," *Migraine* 4(3):36-52 (2001).

Elkind, A.H., "Interval Therapy of Migraine: The Art and Science," *Headache Quarterly, Current Treatment and Research* 1(4):280-289 (1990).

Elkind, A.H., "The Acute Treatment of Migraine," *Headache Quarterly, Current Treatment and Research* 4(Suppl. 2):4-11 (1993).

Faure, et al., "Le Sumatriptan: Une Nouvelle Molecule Pour le Traitement de la Crise de Migraine," *Lyon Pharmaceutique* 45(8):471-478 (1994).

Feinmann, et al., "Orofacial Neuralgia: Diagnosis and Treatment Guidelines," *Drugs* 46(2):263-268 (1993).

Ferrari, et al., "Clinical and Experimental Effects of Sumatriptan in Humans," *Trends Pharmaco Sci* 14(4):129-133 (Apr. 1993).

Ferrari, et al., "Acute Treatment of Migraine Attacks," *Curr. Opin. Neurol.* 8:237-242 (1995).

Ferrari, et al., "Oral Triptans (serotin $5-HT_{1B/1D}$ agonists) in Acute Migraine Treatment: A Meta-Analysis of 53 Trails," *Lancet* 358:1668-1675 (Nov. 17, 2001).

Foussard-Blanpin, et al., "La Douleur Migraineuse et Son Traitement," *Lyon Pharmaceutique* 47(2):71-80 (1996).

Fowler, et al., "The Clinical Pharmacology, Pharmacokinetics and Metabolism of Sumatriptan," *Eur. Neurol.* 31:291-294 (1991).

Fullerton, et al. "Sumatriptan: A Selective 5-Hydroxytryptamine Recceptor Agonist for the Acute Treatment of Migraine," *The Annals of Pharmacotherapy* 26(6):800-808 (Jun. 1992).

Gallagher, R.M., "Appropriate Uses of Abortive Medications in Headache Patients," *Headache Quarterly, Current Treatment and Research* 4(1):23-29 (1993).

Gandini, et al., "First Dose and Steady State Pharmacokinetics of Nimesulide and Its 4-Hydroxy Metabolite in Healthy Volunteers," *Farmaco* 46(9):1071-1079 (1991).

King, F.D., Medicinal Chemistry: Principles and Practice. London: *The Royal Society of Chemistry* p. 265-277 (1999).

King, et al., Tablets, Capsules, and Pills; Coating of Pharmaceutical Dosage Forms; Prolonged-Action Pharmaceuticals; and The Prescription, *Remington's Pharmaceutical Sciences* 1980, at 1553, 1585, 1721-1725 and 1600 (Arthur Osol ed.).

Lance, J.W., "Chronic Headache: A Guide to Successful Management," *Modern Medicine of Australia* 12-18 (Jan. 1993).

Lumen, et al., "Adverse Reactions Associated with Sumatriptan," *Lancet* 341:1091-1092 (Apr. 24, 1993).

Lundberg, P.O., "Treatment of Headache in Norway and Sweden," *Headache Quarterly, Current Treatment and Research* 6(2):102-112 (1995).

Macor, et al., "3-(1,2,5,6-tetrahydropyrid-4-yl)pyrrolo[3,2-b]byrid-5-one: A Potent and Selective Serotonon ($5-HT_{1B}$) Agonist and Rotationally Restricted Phenolic analog of 5-methoxy-3-(1,2,5,6-tetrahydropyrid-4-yl)indole," *J. Med. Chem.* 33:2087-2093 (1990).

Marterer, et al., "Die Medikamentose Therpie Der Migrane Ein Literaturuberblick," *Fortschr. Neurolo. Psychiat.* 63:1-16 (1995).

Matthew, et al., "Coexistence of Migraine and Idiopathic Intracranial Hypertension Without Papilledema," *Neurol.* 46(5):1226-1230 (May 1996).

Matthew, N.T., "Transformed Migraine, Analgesic Rebound, and Other Chronic Daily Headaches," *Neurol. Clin.* 15(1):167-186 (Feb. 1997).

Matthew, N.T., "Serotonin 1D (5-HT1D) Agonists and Other Agents in Acute Migraine," *Neurol. Clin.* 15(1):61-83 (Feb. 1997).

Matthew, et al., "Headache After Frequent Triptan Use," *Lancet* 353:1363-1364 (Apr. 17, 1999).

McAlhany, A., "Efficacy of Sumatriptan in the Treatment of Migraine: A Review of the Literature," *J. Neurosci. Nurs.* 33(5):270-277 (Oct. 2001).

Meschia, et al., "Reversible Segmental Cerebral Arterial Vasopasm and Cerebral Infraction: Possible Association with Excessive Use of Sumatriptan and Midrin," *Arch. Neurol.* 55(5):712-714 (May 1998).

Moskowitz, et al., "Sumatriptan: A Receptor-Targeted Treatment for Migraine," *Annu. Rev. Med.* 44:145-154 (1993).

Noack, et al., "Migraine: Definitions, Mechanisms, and Treatment," *South Med. J.* 89(8):762-769 (Aug. 1996).

Pini, et al., "Headaches Associated With Chronic Use of Analgesics: A Therapeutic Approach," *Headache* 36(7):433-439 (1996).

Pini, et al., "Treating Headaches Associated With Chronic Analgesic Use," *Reactions Weekly* 617:2 (No later than Sep. 16, 1996).

Putnam, et al., "Migraine Polypharmacy and the Tolerability of Sumatriptan: A Large-Scale, Prospective Study," *Cephalalgia* 19:668-675 (1999).

Raskin, et al., "Approach to the Patient With Migraine," *Hosp. Pract.* (Minneap) 31(2):93-96, 101-104 (Feb. 1996).

Rothrock, J.F., "Successful Treatment of Persistent Migraine Aura With Divalproex Sodium," *Neurol* 48(1):261-262 (Jan. 1997).

Schoenen, et al., "Self-Treatment of Acute Migraine With Subcutaneous Sumatriptan Using an Autoinjector Device: Comparison With Customary Treatment in an Open, Longitudinal Study," *Cephalalgia* 14(1):55-63 (1994).

Shane, R., "Development and Implementation of Practice Guidelines (Part I)," *Hosp. Formul.* 29:711-719 (Oct. 1994).
Sheftell, F.D., "Role and Impact of Over-the-Counter Medications in the Management of Headache," *Neurol. Clin.* 15(1):187-198 (Feb. 1997).
Silberstein, et al., "Safety and Efficacy of Ergotamine Tattrate and Dihydroergotamine in the Treatment of Migraine and Status Migrainous," *Neurology* 45(3 Pt 1):577-584 (Mar. 1995).
Silberstein, S.D., "Overview of Diagnosis and Treatment of Migraine," *Neurol.* 44(10 Suppl. 7):S6-S16 (Oct. 1994).
Skaer, T.L., "Clinical Presentation and Treatment of Migraine," *Clin. Ther.* 18(2):229-245; discussion 228; (Mar.-Apr. 1996).
Solomon, G.D., "Treatment Consideration in Headache and Associated Medical Disorders," *J. Pain System Manage.* 8(2):73-80 (1993).
Srinivasu, et al., "Lack of Pharmacokinetic Interaction Between Sumatriptan and Naproxen," *J. Clin. Pharmacol.* 40:99-104 (2000).
Swain, et al., "Diagnosis, Prophylaxis and Treatment of Headaches in the Athlete," *South Med. J.* 90(9):878-888 (Sep. 1997).
Tansey, et al., "Sumatriptan in the Acute Treatment of Migraine," *J. Neurol. Sci.* 114:109-116 (1993).
Tfelt-Hansen, P., "Drug Treatment of Migraine: Acute Treatment and Migraine Prophylaxis," *Curr. Opin. Neurol.* 9(3):211-213 (Jun. 1996).
Tfelt-Hansen, et al., "Tth Effectiveness of Combined Oral Lysine Acetylsalicylate and Metoclopramide Compared With Oral Sumatriptan for Migraine," *Lancet* 346:923-926 (Oct. 7, 1995).
Tfelt-Hansen, P, "Prophylatic Pharmacotherapy of Migrane; Some practical Guidelines," *Neurol. Clin.* 15(1):153-165 (Feb. 1997).
Thomas, et al., "Emergency Department Treatment of Migraine, Tension and Mixed-Type Headache," *J. Emerg. Med.* 12(5):657-664 (1994).
Uzogara, et al., "A Combination Drug Treatment for Acute Common Migraine," *Headache* 26:231-236 (May 1986).
Visser, et al., "Sumatriptan in Clinical Practice: A 2-Year Review of 453 Migraine Patients," *Neurol.* 47(1):46-51 (Jul. 1996).
Visser, et al., "Chest Systoms After Sumatriptan: A 2-Year Clinical Practice Review in 735 Consecutive Migraine Patients," *Cephalalgia* 16(8):554-559 (Dec. 1996).
Visser, et al., "Rizatriptan vs. Sumatriptan in the Acute Treatment of Migraine," *Arch. Neurol.* 53:1132-37 (Nov. 1996).
Von Korff, et al., "Headache Medication—Use Among Primary Care Headache Patients in a Health Maintenance Organization," *Cephalalgia* 19:575-80 (1999).
Welch, K.M.A., "The Therapeutics of Migraine," *Curr. Opin. Neurol. Neurosurg.* 6(2):264-269 (Apr. 1993).
Wiedemann, et al., "Effects of Antimigraine Drugs on Retinal Spreading Depression," *Naunyn Schmiedebergs Arch Pharmacol* 353(5):552-556 (Apr. 1996).
Wilkinson, M., "Migraine Treatment, the British Perspective," *Headache* 34(8):S13-S16 (Sep. 1996).
European Search Report for EP03808537.9.
International Search Report for PCT/US00/03897.
Toradol® IM and Toradol® Oral (ketorolac tromethamine); Physicians' Desk Reference, 49th Ed. pp. 2492-2496.
Naprosyn® (naproxen) tablets and suspension; Physicians' Desk Reference, 48th Ed. pp. 2350-2352 and 2363-2365.
Piroxicam, Merck Index, 13th Ed., p. 1346 (2001).
Imitrex tablets, labeling approved Jun. 1, 1995.
21 U.S.C. § 355(b)(1)(F).
21 C.F.R. § 201.
Imitrex injections, labeling approved Dec. 28, 1992.
Various Program Abstracts. 28th Annual Meeting of the American Association for the Study of Headache, presented Jun. 27-29, 1986, Chicago, IL.
Certified English language translation of Faure scientific article.
Certified English language translation of Foussard-Blanpin, et al. scientific article.
Certified English language translation of Marterer, et al. scientific article.
Adam E.I., "A Treatment for the Acute Migraine Attack," *J Int Med Res* 15(2):71-75 (1987).

*ad hoc* committe, Principles of Pharmacology: Basic Concepts & Clinical Applications (Paul L. Munson ed., Chapman & Hall, New York) (1995), pp. 44, 563-65, 1166-78, 1659-60.
Boureau F., et al., "Doulbe-blind comparison of an acetaminophen 400 mg-codeine 25 mg combination versus asprin 1000mg and placebo in acute migraine attack," *Cephalalgia* 14(2):156-161 (Apr. 1994).
Chabriat H., et al. "Combined oral lysine acetylsalicylate and metoclopramide in the acute treatment of migraine: a multicentre double-blind placebo-controlled study," *Cephalalgia* 14(4):297-300 (Aug. 1994).
Charles, A., et al., "Commentary: Sumatriptan-naproxen combination for acute migraine," *Nature Clinical Practice Neurology* 3(11):604-605 (Nov. 2007).
Diamond S., "Treatment of migraine with isometheptene, acetaminophen, and dichloralphenazone combination: a double-blind, crossover trail," *Headache* 15(4):282-287 (Jan. 1976).
Dowson A., et al., "Comparison of a Fixed Combination of Doperidone and Paracetamol (Domperamol) with Sumatriptan 50 mg in Moderate to Severe Migraine: A Randomised UK Primary Care Study," *Curr. Med. Res. Opin.* 16(3):190-197 (2000).
Friedman, A.P., et al., "Fiorinal® with Codeine in the Treatment of Tension Headache—the Contribution of Components to the Combination Drug," Clin Thet 10(3):303-315 (1988).
Goldstein J., et al., "Treatment of severe, disabling migraine attacks in an over-the-counter population of migraine suffers: results from three randomized, placebo-controlled studies of the combination of acetaminophen, asprin, and caffeine," *Cephalalgia* 19(7):684-691 (1999).
Hakkarainen H., et al., "Ergotamine vs. Metoclopramide vs. Their Combination in Acute Migraine Attacks," *Headache* 22(1):10-12 (Jan. 1982).
Hakkarainen H., et al., "Mild analgesics as an alternative to ergotamine in migraine. A comparative trial with acetysalcyclic acid, ergotamine tartrate, and dextropropoxyphene compound," *J Clin. Pharmacol.* 20(10):590-595 (1980).
Klapper J.A., et al., "Ketorolac versus DHE and Metoclopramide in the Treatment of Migraine Headaches," *Headache* 31(8):523-524 (Sep. 1991).
Le Junne C., et al., "Comparative Efficacy and Safety of Calcium Carbasalate plus Metoclopramide versus Ergotamine Tartrate plus Caffeine in the Treatment of Acute Migraine Attacks," *Eu.r Neurol.* 41(1):37-43 (1999).
MacGregor E.A., et al., "Domperidone plus paracetamol in the treatment of migraine," *Cephalalgia* 13(2):124-127 (Apr. 1993).
Nappi G., et al.," Oral sumatriptan compared with placebo in the acute treatment of migraine," *J. Neurol.* 241 (© Springer-Verlag) pp. 138-144 (1994).
Nestvold K., et al., "Treatment of acute migraine attack: naproxen and placebo compared," *Int'l J. of Headache* 5(2):115-119 (Jun. 1985).
Pradelier A., et al., "Calcium carbasalate-metoclopramide combination versus dihydroergotamine in the treatment of migraine attacks," *Pathol Biol* (Paris) 43(9):806-813, including English Abstract and English translation of pp. 807-812 (1995).
Ryan R.E., "Double-blind clinical evaluation of the efficacy and safety of ergostine-caffeine, and placebo in migraine headaches," *Headache* 9(4):212-220 (Jan. 1970).
Scherl, E.R., et al., "Comparison of Dihydroergotamine With Metoclopramide Versus Meperidine With Promethazine in the Treatment of Acute Migraine," *Headache* 35(5):256-259 (May 1995).
Silberstein S.D., et al., "Treatment of Menstruation-Associated Migraine with the Nonprescription Combination of Acetaminophen, Asprin, and Caffeine: Results from Three Randomized, Placebo-Controlled Studies," *Clin. Ther.* 21(3):475-491 (1991).
Somerville, B.W., "Treatment of Migraine Attacks with an Analgesic Combination (Mersyndol)," *Med. J. Aust.* 1(23):865-866 (Jun. 1976).
Subcutaneous Sumatriptan International Study Group," Treatment of Migraine Attacks with Sumatriptan," *New England J. of Medicine* 325(5):316-321 (Aug. 1, 1991).
Tfelt-Hansen P., et al., "Effervescent metoclopramide and asprin (Migravess) versus effervescent asprin or placebo for migraine attacks: a double-blind study," *Cephalalgia* 4(2):107-111 (1984).

Von Korff M., et al., "Headache medication-use amoung primary care headache patients in a health maintenance organization,"Cephalalgia 19:575-580 (1999).

Yuill G.M., et al., "A Double-blind Crossover Trial of Isometheptene mucate Compound and ergotamine in Migraine," Br. J. Clin. Pract. 26(2):76-79 (Feb. 1972).

Anaprox® (naproxen sodium) tablets, Physician's Desk Reference (46th ed.) pp. 2288-2290 (1992).

Cafergot® (ergotamine tatrate and caffeine) tablets and suppositories, Physician's Desk Reference (46th ed.) pp. 1999-2000 (1992).

Isocom® (isometheptene mucate, dichloraphenzone, and acetaminophen) capsule, Physician's Desk Reference (46th ed.) p. 1629 (1992).

Midrin® (isometheptene mucate, dichloraphenzone, and acetaminophen) capsules, Physician's Desk Reference (46th ed.) p. 836 (1992).

Wigraine® (ergotamine tatrate and caffeine) tablets, Physician's Desk Reference (46th ed.) p. 1645 (1992).

Naprosyn® (naproxen) tablets and suspension, Physician's Desk Reference (46th ed.) pp. 2297-2299 (1992).

Imitrex® injection (sumatriptan succinate), Physician's Desk Reference (49th ed.) pp. 855-858 (1995).

Imitrex® (tablet) Prescribing Information: labeling approved Jun. 1, 1995.

Imitrex® Approval Letter, Jun. 1, 1995.

Regulatory Approvals for Naproxen and Naproxen Sodium.

Regulatory Approvals for Sumatriptan.

Pozen Inc.'s Reply to Defendant Par Pharmaceutical Inc.'s, Counterclaims, filed Dec. 29, 2008.

Plaintiff Pozen Inc.'s Original Complaint against Alphapharm Pty Ltd., Mylan Pharmaceuticals Inc. and Mylan Inc., filed Jan. 2, 2009 with Exhibits A and B.

Plaintiff Pozen Inc.'s First Amended Complaint against Alphapharm Pty Ltd., filed Jan. 29, 2009.

Plaintiff Pozen Inc.'s Answer to Amended Complaint and Counterclaim against Alphapharm Pty Ltd., filed Feb. 20, 2009.

Plaintiff Pozen Inc.'s Disclosure of Asserted Claims and Infringement Contentions Under Patent Rule 3-1, Against Par Pharmaceutical Inc., filed Mar. 9, 2009.

Pozen Inc.'s Reply to Defendant Alphapharm Pty Ltd.'s Counterclaims, filed Mar. 16, 2009.

Defendant Par Pharmaceutical, Inc.'s Amended Answer and Counterclaims, filed Mar. 17, 2009.

Defendant Alphapharm's Initial Disclosures Pursuant to Section 1 of the Discovery Order and Fed. R. Civ. P. Rule 26(a)(1), filed Apr. 17, 2009.

Defendant Par Pharmaceutical, Inc.'s Initial Disclosures, filed Apr. 17, 2009.

Plaintiff Pozen Inc.'s Initial Disclosures, filed Apr. 17, 2009.

Plaintiff Pozen Inc.'s Original Complaint against Teva Pharmaceuticals USA, Inc., filed Apr. 24, 2009 with Exhibits A and B.

Alphapharm's Amended Answer to Amended Complaint and Counterclaim, filed May 13, 2009.

Teva Pharmaceuticals USA, Inc.'s Answer and Counterclaims to Pozen Inc.'s Original Complaint, filed May 18, 2009.

Pozen Inc.'s Reply to Defendant Teva Pharmaceuticals USA, Inc.'s Counterclaims, filed Jun. 8, 2009.

Pozen Inc.'s Reply to Defendant Alphapharm Pty Ltd.'s Amended Counterclaims, filed Jun. 26, 2009.

Plaintiff Pozen Inc.'s Disclosure of Asserted Claims and Infringement Contentions Under Patent Rule 3-1, Against Teva Pharmaceuticals USA, Inc. filed Jul. 2, 2009.

Plaintiff Pozen Inc.'s Amended Complaint against Teva Pharmaceuticals USA, Inc., filed Jul. 6, 2009 with Exhibits A, B and C.

Defendant Par Pharmaceutical, Inc.'s First Set of Requests for Admission (Nos. 1-4) to Pozen, filed Jul. 24, 2009.

Plaintiff Pozen Inc.'s Initial Disclosures, filed Aug. 7, 2009.

Defendant Teva Pharmaceuticals USA, Inc.'s Initial Disclosures, filed Aug. 7, 2009.

Pozen Inc.'s Reply to Defendant Teva Pharmaceuticals USA, Inc.'s Answer and Counterclaims to Pozen Inc.'s Amended Complaint, filed Aug. 13, 2009.

Plaintiff Pozen Inc.'s Amended Complaint Against Par Pharmaceutical Inc., Alphapharm Pty Ltd., Teva Pharmaceuticals USA, Inc. and Dr. Reddy's laboratories Inc., filed Aug. 21, 2009 with Exhibits A, B and C.

Plaintiff Pozen Inc.'s Responses and Objections to Defendant Par Pharmaceutical, Inc.'s First Set of Requests for Admission (Nos. 1-4) to Pozen, filed Aug. 26, 2009.

Plaintiff Pozen Inc.'s Disclosure of Asserted Claims and Infringement Contentions Under Patent Rule 3-1, filed Sep. 3, 2009.

Alphapharm PTY Ltd.'s Answer to Pozen Inc.'s Amended Complaint and Counterclaims, filed Sep. 23, 2009.

Dr. Reddy's Laboratories, Inc.'s Answer, Affirmative Defenses and Counterclaim to Pozen Inc.'s Amended Complaint, filed Sep. 23, 2009.

Par's Answer and Counterclaims to Amended Complaint, filed Sep. 23, 2009.

Teva Pharmaceuticals USA, Inc.'s Answer and Counterclaims to Pozen Inc.'s [Second] Amended Complaint, filed Sep. 23, 2009.

Plaintiff Pozen Inc.'s Initial Disclosures, filed Sep. 25, 2009.

Defendant Par Pharmaceutical, Inc.'s Second Set of Interrogatories to GlaxoSmithKline Nos. (10-12), filed Sep. 29, 2009.

Teva Pharmaceuticals USA, Inc.'s First Set of Interrogatories to Plaintiff, filed Oct. 2, 2009.

Alphapharm PTY Ltd.'s Objections and Responses to Plaintiff Pozen Inc.'s First Set of Interrogatories to Defendant Alphapharm PTY LTD. (Nos. 1-2), filed Oct. 5, 2009.

Teva Pharmaceuticals USA, Inc.'s Answers to Pozen's First Set of Interrogatories (Nos. 1-2), filed Oct. 5, 2009.

Defendant Par Pharmaceutical, Inc.'s Objections and Responses to Plaintiff Pozen Inc.'s First Set of Interrogatories (Nos. 1-2), filed Oct. 5, 2009.

Pozen Inc.'s Reply to Defendant Alphapharm PTY Ltd.'s Answer and Counterclaims to Pozen Inc.'s Amended Complaint, filed Oct. 16, 2009.

Pozen Inc.'s Reply to Defendant Dr. Reddy's Laboratories, Inc.'s Answer, Affirmative Defenses and Counterclaim to Pozen Inc.'s Amended Complaint, filed Oct. 16, 2009.

Pozen Inc.'s Reply to Defendant Par Pharmaceutical, Inc. Answer and Counterclaims to Pozen Inc.'s Amended Complaint, filed Oct. 16, 2009.

Pozen Inc.'s Reply to Defendant Teva Pharmaceuticals USA, Inc.'s Answer and Counterclaims to Pozen Inc.'s [Second] Amended Complaint, filed Oct. 16, 2009.

Plaintiff Pozen Inc.'s Disclosure Under Local patent Rule 4-2 of Preliminary Claim Constructions and Extrinsic Evidence, filed Oct. 23, 2009.

Dr. Reddy's Laboratories, Inc.'s Answer, Affirmative Defenses and Counterclaim to Pozen Inc.'s Amended Complaint, filed Oct. 27, 2009.

Plaintiff Pozen Inc.'s Objections and Responses to Defendant Teva Pharmaceuticals USA, Inc.'s First Set of Interrogatories to Plaintiff, filed Nov. 4, 2009.

Plaintiff Pozen Inc.'s Responses and Objections to Defendant Teva Pharmaceuticals USA, Inc.'s First Set of Requests for Admission to Plaintiff, filed Nov. 4, 2009.

Pozen Inc.'s Reply to Defendant Dr. Reddy's Laboratories, Inc.'s Answer, Affirmative Defenses and Counterclaim to Pozen Inc.'s Amended Complaint, filed Nov. 13, 2009.

GlaxoSmithKline's Responses to Defendant Alphapharm Pty Ltd.'s First Set of Interrogatories to GlaxoSmithKline (Nos. 1-12), filed Sep. 18, 2009.

GlaxoSmithKline's Supplemental Responses to Defendant Par Pharmaceutical, Inc.'s Interrogatories to GlaxoSmithKline Nos. 2, 3 & 9, filed Sep. 30, 2009.

GlaxoSmithKline's Supplemental Responses to Defendant Par Pharmaceutical, Inc.'s Interrogatory to GlaxoSmithKline No. 1, filed Oct. 23, 2009.

GlaxoSmithKline's Responses to Defendant Par Pharmaceutical, Inc.'s Second Set of Interrogatories to GlaxoSmithKline (Nos. 10-12), filed Oct. 23, 2009.

GlaxoSmithKline's Responses and Objections to Defendant Par Pharmaceutical, Inc.'s Notice of Deposition to GlaxoSmithKline Pursuant to Fed. R. Civ. P. 30(B)(6), filed Nov. 9, 2009.

Par's Amended Answer and Counterclaims to Amended Complaint, filed Nov. 25, 2009.
Preliminary Invalidity Contentions (including Exhibits 1, 2, 2A, 2B, 2C, 2D, 2E, 3, 3A, 4 &4A) of Dr. Reddy's laboratories Inc., filed Oct. 19, 2009.
Pozen Inc.'s Objections and Responses to Alphapharm Pty Ltd.'s First Set of Interrogatories (Nos. 1-26) dated Aug. 10, 2009.
Pozen's Inc.'s Objections and Responses to Par Pharmaceutical Inc.'s First Set of Interrogatories (Nos. 1-10) dated Aug. 10, 2009.
Pozen Inc.'s Reply to TEVA Pharmaceuticals USA, Inc.'s Answer and Counterclaims to Pozen Inc.'s Amended Complaint dated Aug. 13, 2009.
Pozen Inc.'s Amended Complaint with Exhibits A-C dated Aug. 21, 2009.
Pozen's Inc.'s Responses and Objections to Par Pharmaceutical Inc.'s First Set of Requests for Admission (Nos. 1-4) dated Aug. 26, 2009.
GlaxoSmithKline's Responses to Defendant Par Pharmaceutical Inc.'s First Set of Requests for Admission (Nos. 1-4) dated Sep. 3, 2009.
Pozen's Disclosure of Asserted Claims and Infringement Contentions Under Patent Rule 3-1 dated Sep. 3, 2009.
GlaxoSmithKline's Responses to Defendant Par Pharmaceutical Inc.'s First Set of Interrogatories to GlaxoSmithKline (Nos. 1-9) dated Sep. 10, 2009.
Charles, et al. Commentary, "Sumatriptan-Naproxen Combination for Acute Migraine," *Nature Clinical Practice Neurology* 3)11):604-605 (Nov. 2007).
Letter sent to Applicant dated Apr. 14, 2009 (2 pages), including: Paragraph IV Certification Statement of the Factual and Legal Bases for Concluding that US 6,060,499, US 6586,458 and US 7,332183 are Invalid, Unenforceable or Not Infringed (25 pages); and Offer of Confidential Access (4 pages), with copies of the following references attached: a) Saadah, *Headache* 32:95-97 (1992), b) Mathew, *Headache* 26:314 (1986); c) Plosker, et al., *Drugs* 47:622-651 (1994); d) Welch, *New Eng. J. Med.* 329:1476-1483 (1993); e) Leone, et al., *Ital. J. Neurol. Sci.* 16:577-586 (1993); f) Brandes, et al., *J. Am. Med. Assoc.* 297:1443-1454 (2007); g) Smith, et al., *Headache* 45:983-991 (2007); h) Gross, *Exp. Opin. Invest. Drugs* 4(4):283-290 (1995).
Letter sent to Applicant dated Nov. 20, 2008, Re: Notification of Certification of Noninfringement and/or Invalidity for US Patent Nos. 6,060499, 6,586,458 and 7,332,183 Pursuant to § 505(j)(2)(B)(ii) of the Federal Food, Drug and Cosmetic Act (39 pages), including: Tab 1 (copy of e-mail re use of Federal Express in lieu of US Postal Service); Tab 2 (Saadah, *Headache* 32:95-97 (1992)); Tab 3 (Raskin, *Neurology* 43 (suppl 3):S39-S42 (1993)) and Tab 4 (Imitrex labeling approved Jun. 1, 1992).
Letter sent to Applicant dated Oct. 8, 2008 Re: Treximet™ 119 mg sumatriptan succinate . . . Notice of Paragraph IV Certification, including: a cover letter (2 pages); attachment entitled "Offer of Confidential Access and Confidentiality Agreement Pursuant to 21 U.S.C. §355(i)(5)(C)(i)(III)" (8 pages); Detailed Statement of the Factual and Legal Bases for the Opinion of . . . . that US Patent Nos. 6,060,499, 6,586,458 and 7,332,183 are Invalid, Unenforceable, and/or Will not be Infringed (39 pages); and Appendix of Pertinent Principles of Patent Law (16 pages); with copies of the following references attached: a) Tfelt-Hansen, *Cephalalgia* 13:238-244 (1993); b) Mathew, *Headache* 26:314 (1986); c) Saadah, *Headache* 32:95-97 (1992); d) Kumar, et al., "Headaches," *Medical Clinics of North America* 79(2):261-286 (Mar. 1995); e) Solomon, *Seminars in Pediatric Neurology* 2(2):165-177 (Jun. 1995); f) Hoernecke, et al., *Medizinische Klinik* 88:642-648 (1993) (abstract).
Gross, *Exp. Opin. Invest. Drugs* 4:283-290 (1995).
Notice of Paragraph IV Certification Re: Naproxen Sodium/Sumatriptan Succinate Tablets dated Jul. 31, 2009.
Pozen Inc.'s Original Complaint against Teva Pharmaceuticals USA filed Apr. 24, 2009 with Exhibit A and Exhibit B.
Teva Pharmaceuticals USA, Inc.'s Answer and Counterclaims to Pozen Inc.'s Original Complaint; filed May 18, 2009.
Pozen Inc.'s Amended Complaint against Teva Pharmaceuticals USA, Inc.; filed Jul. 6, 2009 with Exhibits A, B and C.

Teva Pharmaceuticals USA, Inc.'s Answer and Counterclaims to Pozen Inc.'s Amended Complaint; filed Jul. 27, 2009.
Wade, A., et al., "Handbook of Pharmaceutical Excipients", American Pharmaceutical Association (1994).
Invalidity Contentions filed with the US District Court for the Eastern District of Texas, Tyler Division, by a Defendant on May 13, 2009 in which arguments are presented that claims in US 6,060,499, US 6586,458 and US 7,332,183 are invalid or unenforceable (36 pages) along with Exhibit A (2 pages); Exhibit B (61 pages); Exhibit C (63 pages); and Exhibit D (70 pages).
Invalidity Contentions filed by a second Defendant with with the US District Court for the Eastern District of Texas, Tyler Division, on May 13, 2009 in which arguments are presented that claims in US 6,060,499, US 6586,458 and US 7,332,183 are invalid or unenforceable (81 pages) along with Exhibit A (66 pages).
Invalidity Contentions filed with the US District Court for the Eastern District of Texas, Tyler Division, by a Defendant on Aug. 14, 2009 in which arguments are presented concerning the claims in US 6,060,499, US 6586,458 and US 7,332,183 (61 pages) along with Exhibit A (69 pages) and Defendant's Notice of Compliance (3 pages).
Invalidity Contentions filed with the US District Court for the Eastern District of Texas, Tyler Division, by a Defendant on May 13, 2009 in which arguments are presented that claims in US 6,060,499, US 6586,458 and US 7,332,183 are invalid or unenforceable (36 pages) along with Exhibit A (2 pages); Exhibit B (61 pages); Exhibit C (63 pages); Exhibit D (70 pages) and Exhibit E (43 pages).
Alphapharm's Amended Answer to Amended Complaint and Counterclaim, filed with the District Court for the Eastern District of Texas, Tyler Division on May 13, 2009 in Civil Action No: 6:08-cv-437 (LED) (consolidated with Civil Action No:6:09-cv-3).
*Pozen, Inc.* v. *Par Pharmaceutical, Inc.*—Order Granting Unopposed Motion to Consolidate this Patent Infringement Action with 6:09-cv-003-LED, filed Feb. 10, 2009.
*Pozen, Inc.* v. *Alphapharm Pty Ltd.*—Answer to Amended Complaint and Counterclaim, filed Feb. 20 2009.
Pozen Inc.'s Post-Trial Brief with Exhibits A-G, filed Nov. 17, 2010.
Defendants' Initial Post-Trial Brief filed Nov. 17, 2010.
Pozen Inc.'s Responsive Post-Trial Brief with Exhibit A, filed Nov. 24, 2010.
Defendants' Responsive Post-Trial Brief (Filed Under Seal) with Exhibit 1, filed Nov. 24, 2010.
Deposition of Henry G. Grabowski, Ph.D. dated Jul. 30, 2010 with Exhibit "Grabowski 1" and Exhibits 390-396.
Deposition of Andrew M. Blumenfeld, M.D. (Day 1) dated Aug. 2, 2010 with Exhibits 397-402.
Deposition of Andrew M. Blumenfeld, M.D. (Day 2) dated Aug. 4, 2010 with Exhibits 403-405, 409 and 411-418.
Deposition of Keith Leffler, Ph.D. dated Aug. 10, 2010 with Exhibits 1-11.
Deposition of Robert O. Williams III, Ph.D. (vol. 1) dated Aug. 18, 2010 with Exhibits 419-426.
Deposition of Robert O. Williams III, Ph.D. (vol. 2) dated Aug. 20, 2010 with Exhibits 427-432.
Second Supplemental Expert Report of Andrew M. Blumenfeld, M.D. dated Aug. 23, 2010 with Exhibits 1-9.
Supplemental Expert Report of Keith B. Leffler, Ph.D. dated Aug. 23, 2010 with Charts 1, 3, 4 and 5 and Exhibit A.
Fifth and Supplemental Expert Report of Nabih M. Ramadan, M.D. dated Sep. 8, 2010.
Deposition of Nabih M. Ramadan, M.D. (Day 1) dated Sep. 9, 2010 with Exhibits 1-7.
Deposition of Nabih M. Ramadan, M.D. (Day 2) dated Sep. 10, 2010 with Exhibits 8-16.
Deposition of Andrew Blumenfeld, M.D. dated Sep. 20, 2010.
Deposition of Patrick J. Sinko, Ph.D. dated Sep. 22, 2010 with Exhibits 1-9.
Protocol Amendrnent/TXA107979 dated Nov. 18, 2009 (also included with Second Supplemental Expert Report of Andrew M. Blumenfeld, M.D.
TXA107979 Results Synopsis dated Jul. 27, 2010 (also included with Second Supplemental Expert Report of Andrew M. Blumenfeld, M.D.

Protocol TXA107979 (also included with Second Supplemental Expert Report of Andrew M. Blumenfeld, M.D.
Sumatriptan and Naproxen Sodium Tablets Rx only (also included with Deposition of Patrick J. Sinko, Ph.D.
Par Pharmaceutical, Inc.'s Motion to Exclude the Testimony of Thomas G. Wiseman, Esq. with Exhibits A, B Part 1 and B Part 2.
Defendants' Motion for Partial Summary Judgment of Invalidity of U.S. Patent No. 6,060,499 dated Aug. 25, 2010 with Exhibits A-I.
Plaintiff Pozen Inc.'s Findings of Fact and Conclusions of Law dated Sep. 10, 2010.
Defendants' Proposed Findings of Fact and Conclusions of Law dated Sep. 10, 2010 with Exhibits A-I.
Pozen Inc.'s Brief in Opposition to Par Pharmaceutical, Inc.'s Motion to Exclude the Testimony of Thomas G. Wiseman, Esq. dated Sep. 13, 2010.
Plaintiff's Response in Opposition to Defendants' Motion for Partial Summary Judgment of Invalidity of U.S. Patent No. 6,060,499, dated Sep. 13, 2010 with Exhibits A, A1-A7, B and C.
Plaintiff Pozen Inc.'s Sur-Reply to Defendants' Motion for Partial Summary Judgment of Invalidity of U.S. Patent No. 6,060,499, dated Sep. 24, 2010 with Exhibits A and B.
Par Pharmaceutical, Inc.'s Reply Brief in Support of Its Motion to Exclude the Testimony of Thomas G. Wiseman, Esq. dated Sep. 23, 2010.
Defendants' Reply in Support of Their Motion for Partial Summary Judgment of Invalidity of U.S. Patent No. 6,060,499, dated Sep. 23, 2010.
Defendants' Supplemental Proposed Findings of Fact and Conclusions of Law dated Oct. 1, 2010.
Axert® (alomotriptan malate) Tablets, Highlights of Prescribing Information, Initial U.S. Approval: 2001.
Defendant's Pretrial Objections dated Sep. 29, 2010 with Exhibits A and B.
Plaintiff Pozen Inc's Pretrial Objections dated Sep. 29, 2010 with Exhibit A.
Plaintiff and Defendants Joint Claim Construction and Prehearing Statement with Exhibits 1-3 filed Dec. 8, 2009.
Plaintiff and Defendants Amended Joint Claim Construction and Prehearing Statement with Exhibits 1-3 filed Jan. 7, 2010.
The American Heritage Dictionary of the English Language: Second College Edition (1982); pp. 71, 85, 303, 400, 525, 716, 741, 910, 989, 1084, 1085, 1232, 1328 and 1376.
The American Heritage Dictionary of the English Language: Fourth College Edition (2000); pp. 23, 180, 643, 664, 890, 994, 1155, 1215, 1325, 1450, 1532, 1572, 1587 and 1625.
Collins English Dictionary: Fourth Edition, HarperCollins Publishers (2000); p. 879.
The Condensed Chemical Dictionary: Tenth Edition Revised by Gessner G. Hawley, Van Nostrand Reinhold Company Publisher (1981); p. 907.
The Condensed Chemical Dictionary: Tenth Edition Revised by Gessner G. Hawley, Van Nostrand Reinhold Company Publisher (1981); p. 931.
A Dictionary of Pharmacology and Clinical Drug Evaluation by D. R. Laurence & J. R. Carpenter, UCL Press Publisher (1994); pp. 56, 73, 108 and 121.
Dorland's Illustrated Medical Dictionary: 28$^{th}$ Edition, W. B. Saunders Company Publisher (1994); pp. 1055, 1042, 1043 1870, 1608 and 1100.
The Oxford English Dictionary: Second Edition by J. A. Simpson & E. S. C. Weiner vol. VIII, Claredon Press (1989); 734 and 735.
The Random House Dictionary of the English Language: Second Edition Unabridged, Random House, Inc. (1987); p. 1091.
Stedman's Medical Dictionary: 26$^{th}$ Edition, William & Wilkins (1995); pp. 547, 1340, 1341 and 1525.
Stedman's Medical Dictionary: 26$^{th}$ Edition, William & Wilkins (1995); pp. 20, 69, 517, 546, 678, 758, 764, 886, 1102, 1256, 1282, 1300, 1313, 1314, 1340, 1512, 1568, 1692, 1718, 1757, 1758, 1798, 1799 and 1843.
Webster's Third New International Dictionary of the English Language Unabridged, G. & C. Merriam Company, Publishers (1971); pp. 6, 21, 24, 27, 28, 56, 72, 120, 132, 433, 462, 466, 490, 491, 640, 653, 703, 724, 853, 994, 1138, 1229, 1259, 1422, 1423, 1435, 1575, 1576, 1577, 1585, 1617, 1618, 1655, 1694, 1730, 1894, 1905, 1934, 2112, 2123, 2284, 2285, 2286, 2300, 2317, 2372, 2404, 2434, 2435, 2523, 2524, 2634 and 2635.
Aulton, Michael E., Pharmaceutics: The Science of Dosage Form Design, Churchill Livingstone (1988); pp. 300-303; 616-628; 647-677; and 712-724.
Carstensen, Jens T., Pharmaceutics of Solids and Solid Dosage Forms, John Wiley & Sons (1997); pp. 130-181.
Gordon, Roger E., et al., Pharmaceutical Dosage Forms: Tablets, Second Edition, Revised and Expanded, vol. 2, Lieberman, et al. eds., Marcel Dekker, Inc. (1990); pp. 245-348.
Gunsel, William C., et al., Pharmaceutical Dosage Forms: Tablets, Second Edition, Revised and Expanded, vol. 1, Lieberman, et al. eds., Marcel Dekker, Inc. (1989); pp. 247-284.
King, Robert E., et al., eds., Remington's Pharmaceutical Sciences, Seventeenth Edition, Philadelphia College of Pharmacy and Science (1985); pp. 653-666, 1603-1643 and 1650-1653.
Parrott, Eugene L., Pharmaceutical Dosage Forms: Tablets, Second Edition, Revised and Expanded, vol. 2, Lieberman, et al. eds., Marcel Dekker, Inc. (1990); pp. 201-243.
Peck, Garnet E., et al., Pharmaceutical Dosage Forms: Tablets, Second Edition, Revised and Expanded, vol. 1, Lieberman, et al. eds., Marcel Dekker, Inc. (1989); pp. 75-130.
Sheth, Bhogi B., et al., Pharmaceutical Dosage Forms: Tablets, vol. 1, (1980); pp. 109-185.
Guidance for Industry: Dissolution Testing of Immediate Release Solid Oral Dosage Forms, U.S. Department of Health and Human Services, Food and Drug Administration, Center for Drug Evaluation and Research (Aug. 1997); pp. 1-11, A1 and A2.
Naproxen, The Merck Index. 11$^{th}$ Edition, (1989); p. 1014.
Anaprox®, Physicians' Desk Reference, 49$^{th}$ Edition (1995); pp. 2459-2461.
Naprosyn®, Physicians' Desk Reference, 49$^{th}$ Edition (1995); pp. 2478-2480.
Theory and Practice of Industrial Pharmacy, Third Edition, Indian Edition, Varghese Publishing House (1986).
The United States Pharmacopeia: USP 23, The National Formulary NF 18, (1995); 1053-1055.
The United States Pharmacopeia: USP 23, The National Formulary NF 18, (1995); 1791-1793.
Abbott Laboratories v. Baxter Pharmaceutical Products, Inc., 334 F.3d 1274.
In re Gray et al., 19 C.C.P.A. 745, 53 F.2d 520.
In re Herz et al., 537 F.2d 549.
37 C.F.R. Chapter 1 (Jul. 1, 1996 Edition), Sec. 1.75(e)(1).
21 C.F.R. Chapter 1 (Apr. 1, 1996 Edition), pp. 80-82.
21 C.F.R. Chapter 1 (Apr. 1, 1996 Edition), pp. 1, 8-55.
Pozen Inc.'s Reply to Defendant Par Pharmaceutical, Inc.'s Amended Answer and Counterclaims to Pozen's Amended Complaint filed Dec. 10, 2009.
Defendant Dr. Reddy's Laboratories, Inc.'s Responses to Pozen Inc.'s First Set of Interrogatories (Nos. 1-2) filed Dec. 14, 2009.
Defendant Dr. Reddy's Laboratories, Inc.'s Responses to Pozen Inc.'s Second Set of Interrogatories (Nos. 3-12) filed Dec. 14, 2009.
Defendant Par Pharmaceutical, Inc.'s Objections and Responses to Plaintiff Pozen Inc.'s Second Set of Interrogatories to Defendants (Nos. 3-12) filed Dec. 14, 2009.
Alphapharm Pty Ltd.'s Objections and Responses to Plaintiff Pozen Inc.'s Second Set of Interrogatories to Defendants (Nos. 3-12) filed Dec. 14, 2009.
Alphapharm Pty Ltd.'s Objections and Responses to Plaintiff Pozen Inc.'s Third Set of Interrogatories to Defendant Alphapharm Pty Ltd. (No. 13) filed Dec. 14, 2009.
Teva Pharmaceuticals USA, Inc.'s Answers to Pozen's Second Set of Interrogatories (Nos. 3-12) filed Dec. 17, 2009.
Plaintiff Pozen Inc.'s Opening Claim Construction Brief with Exhibits 1-12 filed Jan. 14, 2010.
Defendant' Responsive Claim Construction Brief with Exhibits 1-3 filed Jan. 29, 2010.
Defendants' Motion and Memorandum in Support of Summary Judgment of Indefiniteness of U.S. Patent Nos. 6,060,449 and 6,586,458 Under 35 U.S.C. § 112 ¶ 2 with Exhibits A, B, and C, filed Jan. 29, 2010.

Catarci, et al., Ergotamine-induced headache can be sustained by sumatriptan daily intake, *Cephalalgia* 14:374-375 (1994).
Catarci, et al., "Sumatriptan: Sustained ergotamine-induced headache: case report," *Reactions Weekly* p. 14 (Dec. 17, 1994).
Dahlof, C., "Headache recurrence after subcutaneous sumatriptan," *Lancet* 339:425-426 (Feb. 15, 1992).
Defendants' Joint Preliminary Proposed Claim Constructions and Identification of Extrinsic Evidence Pursuant to Patent Rule 4-2 filed Oct. 23, 2009.
Deposition of Dennis McNamara dated Nov. 18, 2009 and Nov. 20, 2009 with Exhibits 1-64.
Deposition of Paul Ossi dated Nov. 24, 2010 with Exhibits 65-88.
Deposition of John Plachetka dated Dec. 16, 2009 and Dec. 17, 2009 with Exhibits 89-106.
Deposition of Liz Cermak dated Jan. 8, 2010 with Exhibits 107-127.
Deposition of Venkata Kothapalli dated Jan. 12, 2010 and Jan. 13, 2010 with Exhibits 128-149.
Deposition of Donna Gilbert dated Jan. 14, 2010 and Jan. 15, 2010 with Exhibits 150-167.
Deposition of Michelle Lerner dated Jan. 22, 2010 with Exhibits 168-189.
Exhibit 13: MT400 Product Description (also included with deposition of Dennis McNamara).
Exhibit 14: Letter dated Jul. 26, 2000 with some MT400 IND Submission documents (also included with deposition of Dennis McNamara).
Exhibit 34: Pozen Inc. Correspondences (also included with deposition of Dennis McNamara).
Exhibit 42: Fax dated Oct. 15, 2002 with attached Oct. 2, 2002 letter and documents (also included with deposition of Dennis McNamara).
Exhibit 59: Letter dated Apr. 1, 2005 with Pre-NDA Meeting: Briefing Document (also included with deposition of Dennis McNamara).
Exhibit 61: PowerPoint presentation entitled "Neurosciences MDC Trexima: Unique Pharmacokinetic Profile" (also included with deposition of Dennis McNamara).
Exhibit 62: PowerPoint presentation titled "Trexima" (also included with deposition of Dennis McNamara).
Exhibit 65: Study MT-400-201 (also included with deposition of Paul Ossi).
Exhibit 68: Excerpt of NDA 21-926: 2.7.1 Summary of Biopharmaceutics and Associated Analytical Methods (also included with deposition of Paul Ossi).
Exhibit 74: Clinical Study Report MT400-204 (also included with deposition of Paul Ossi).
Exhibit 79: Summary of Clinical Efficacy in Section 2.7.3 of NDA 21-926 (also included with deposition of Paul Ossi).
Exhibit 80: Final Clinical Study Report for MT-400-301 (also included with deposition of Paul Ossi).
Exhibit 83: Prescribing Information for Trexima (also included with deposition of Paul Ossi).
Exhibit 84: Prescribing Information for Trexima (also included with deposition of Paul Ossi).
Exhibit 97: Pozen Inc. The Pharmaceutical Development Company (also included with deposition of John Plachetka).
Exhibit 100: Therapeutic Gain from Study MT400-201/202 documents (also included with deposition of John Plachetka).
Exhibit 153: E-mail dated Jul. 32, 2001 (also included with deposition of Donna Gilbert).
Exhibit 172: MT400: A Sumatriptan/Naproxen Sodium Combination Report (also included with deposition of Michelle Lerner).
Exhibit 173: Letter on Department of Health and Human Services letterhead re NDA 21-926 (also included with deposition of Michelle Lerner).
Exhibit 175: Letter on Department of Health and Human Services letterhead re NDA 21-926 (also included in deposition of Michelle Lerner).
Exhibit 181: Sponsor Signatory Signature Page (also included in deposition of Michelle Lerner).
Exhibit 185: PowerPoint presentation titled Trexima: Early Intervention Studies TRX101998/99 Headline Data (also included in deposition of Michelle Lerner).
Exhibit 187: PowerPoint presentation titled Overview of the Trexima Clinical development program (also included in deposition of Michelle Lerner).
Expert Declaration of Andrew M. Blumenfeld, M.D. with Exhibits 1-6, Filed Feb. 12, 2010.
Reply and Amendment Under 37 C.F.R. § 1.111 and § 1.115 for U.S. Appl. No. 09/151,912 filed Sep. 3, 1999.
Matthew, et al., "Fixed-Dose Sumatriptan and Naproxen in Poor Responders to Triptans With a Short Half-Life," *Headache* 49:971-982 (2009).
Defendant's Responsive Claim Construction Brief with Exhibits 1-3, filed Jan. 29, 2010.
Plaintiff Pozen Inc.'s Reply Claim Construction Brief with Exhibit 1 filed Feb. 12, 2010.
Defendants' Motion and Memorandum in Support of Summary Judgment of Indefiniteness of U.S. Patent Nos. 6,060,499 and 6,586,458 Under 35 U.S.C. § 112 filed Jan. 29, 2010 with Exhibits A-D and Proposed Order Granting Defendants' Motion for Summary Judgment of Indefiniteness of U.S. Patent Nos. 6,060,499 and 6,586,458.
Plaintiff Pozen Inc.'s Memorandum in Opposition to Defendants' Motion and Memorandum in Support of Summary Judgment of Indefiniteness of U.S. Patent Nos. 6,060,499 and 6,586,458 Under 35 U.S.C. § 112 filed Feb. 12, 2010 with Exhibits A, B, C and Proposed Order Denying Defendants' Motion for Summary Judgment of Indefiniteness of U.S. Patent Nos. 6,060,499 and 6,586,458.
Defendant's Reply in Support of Summary Judgment of Indefiniteness of U.S. Patent Nos. 6,060,499 and 6,586,458 Under 35 U.S.C. § 112 filed Feb. 18, 2010 with Exhibits 1-3.
Deposition of Mark Zimmerman dated Feb. 19, 2010 with Exhibits 190-199.
Deposition of Linda Vidette Rouse dated Mar. 10, 2010 with Exhibits 200-234.
Deposition of Susan Elfriede Spruill dated Mar. 18, 2010 with Exhibits 235-250 and 252-260.
Deposition of Robert A. Armitage dated Mar. 24, 2010 with Exhibits 261 and 262.
Deposition of Michael A. Sanzo dated Mar. 26, 2010 with Exhibits 263-268.
Deposition of William Wargin dated Apr. 6, 2010 with Exhibits 269-290.
First Expert Report of Nabih M. Ramadan, M.D. dated Apr. 16, 2010 with Exhibits A-J.
Expert Report of Anthony Palmieri III, Ph.D. dated Apr. 16, 2010 with Exhibits A and B.
Exhibit 196: E-mail dated Jul. 19, 1999 with attachments (also included with deposition of Mark Zimmerman).
Exhibit 197: E-mail dated Sep. 14, 1999 with attachments (also included with deposition of Mark Zimmerman).
Exhibit 198: E-mail dated Nov. 10, 1999 with attachments(also included with deposition of Mark Zimmerman).
Exhibit 199: E-mail dated Jul. 1, 1999 with attachments (also included with deposition of Mark Zimmerman).
Exhibit 200: Slides from Meeting on MT400 dated Jan. 16, 2002 (also included with deposition of Linda Vidette Rouse).
Exhibit 202: Slides from Pozen MT400 Meeting, Apr. 9, 2002 (also included with deposition of Linda Vidette Rouse).
Exhibit 204: Slides from MT400 Meeting of Jun. 13, 2002 (also included with deposition of Linda Vidette Rouse).
Exhibit 209: Pozen, MT400: Report of Jul. 29, 2002 (also included with deposition of Linda Vidette Rouse).
Exhibit 210: Pozen, MT400: a Sumatriptan/ Naproxen Sodium Combination (also included with deposition of Linda Vidette Rouse).
Exhibit 211: MT400 Meeting of Sep. 11, 2002 (also included with deposition of Linda Vidette Rouse).
Exhibit 222: Slides from MT400 Meeting of Apr. 14, 2003 (also included with deposition of Linda Vidette Rouse).
Exhibit 223: Slides from MT400 Meeting of Mar. 24, 2003 (also included with deposition of Linda Vidette Rouse).
Exhibit 225: Pozen MT400 presentation of May 8, 2003 (also included with deposition of Linda Vidette Rouse).
Exhibit 238: Clinical Report dated Mar. 10, 1999 (also included with deposition of Susan Elfriede Spruill).

Exhibit 239: Protocol Amendment dated Feb. 9, 1998 (also included with deposition of Susan Elfriede Spruill).
Exhibit 240: MT400 Protocol dated Feb. 11, 1998 (also included with deposition of Susan Elfriede Spruill).
Exhibit 244: E-mail dated Jan. 30, 2007 (also included with deposition of Susan Elfriede Spruill).
Exhibit 245: MT100-201 Report (also included with deposition of Susan Elfriede Spruill).
Exhibit 246: Correspondence re MT 400 dated Jan. 30, 2007 with associated information (also included with deposition of Susan Elfriede Spruill).
Exhibit 247: Slide Presentation re MT400 beginning with "Overview" (also included with deposition of Susan Elfriede Spruill).
Exhibit 253: Presentation re MT400 beginning with "1996" (also included with deposition of Susan Elfriede Spruill).
Exhibit 254: Presentation beginning with "Overview" (also included with deposition of Susan Elfriede Spruill).
Exhibit 255: Clinical Study from Study MT 400-201/202 (also included with deposition of Susan Elfriede Spruill).
Exhibit 273: E-mail dated Dec. 11, 2003 (also included with deposition of William Wargin).
Exhibit 279: QPS Report (also included with deposition of William Wargin).
Exhibit 280: Pozen Pharmacokinetics Report (also included with deposition of William Wargin).
Exhibit 281: E-mail dated Oct. 7, 2002 (also included with deposition of William Wargin).
Exhibit 283: E-mail dated Feb. 6, 2003 (also included with deposition of William Wargin).
Exhibit 284: E-mail dated Dec. 18, 2002 (also included with deposition of William Wargin).
Exhibit 285: E-mail dated Dec. 2, 2003 (also included with deposition of William Wargin).
Exhibit 288: Graph Figures 13-15 (also included with deposition of William Wargin).
Exhibit 289: E-mail dated Dec. 19, 2002 (also included with deposition of William Wargin).
Alphapharm PTY Ltd.'s Memorandum of Law in Opposition to Pozen Inc.'s Motion to Dismiss the Seventh and Eighth Counts of Alphapharm's Amended Counterclaims with Exhibits A-E filed Jul. 27, 2009.
Pozen Inc.'s Reply Brief in Support of Its Motion to Dismiss the Seventh and Eighth Counts of Alphapharm's Amended Counterclaims with Exhibit A filed Aug. 20, 2009.
Sumatriptan and Naproxen Sodium Tablets Rx Only Issued: Mar. 2010.
Pozen Inc.'s Motion to Dismiss the Seventh and Eighth Counts of Alphapharm's Amended Counterclaims and Brief in Support filed Jun. 26, 2009.
Provisional Claim Construction Order filed Mar. 26, 2010.
Transcript of Markman Hearing dated Feb. 25, 2010.
Deposition of Gary Goodson dated Apr. 23. 2010 with Exhibits 291-313.
Expert Report of Judith Goldberg dated Apr. 15, 2010 with Exhibits 1-3, 5-28 and 29-31.
Expert Report of James Ayers dated May 5, 2010 with Exhibits A-N.
Second Expert Report of Anthony Palmieri III, Ph.D. dated May 5, 2010.
Second Expert Report of Nabih M. Ramadan, M.D., dated May 4, 2010.
Exhibit 303: Clinical Summaries (also included with deposition of Gary Goodson).
Defendant's Motion for Leave to Amend Their Invalidity Contention with Exhibits A-C, dated Apr. 16, 2010.
Par's Second Amended Answer and Counterclaims to Amend Complaint, dated May 14, 2010.
Defendant's Motion to Clarify Mar. 26, 2010 Provisional Claim Construction Order, dated Apr. 29, 2010.
Defendant's Reply to Pozen, Inc's Brief in Opposition to Defendants' Motion for Leave to Amend Their Invalidity Contentions, dated May 13, 2010.
Pozen Inc.'s Response to Defendant's Notice of Mootness, dated May 13, 2010.
Plaintiff Pozen Inc.'s Supplemental Initial Disclosures, dated May 13, 2010.
Deposition of Chris Gennings dated Jun. 12, 2010 with Exhibits 382-386.
Deposition of Thomas G. Wiseman dated Jun. 17, 2010 with Exhibits 387-389.
Deposition of Dr. Nabih Ramadan dated Jun. 24, 2010 with Exhibits 1-4.
Defendants' Notice of Erratum Concerning Their Amended Invalidity Contentions dated Jun. 25, 2010 with Exhibit A.
458 Patent Infringement Report of Andrew M. Blumenfeld, M.D. (Alphapharm Pty Ltd.) dated Jun. 25, 2010 with Exhibits 1-22.
499 Patent Infringement Report of Andrew M. Blumenfeld, M.D. (Alphapharm Pty Ltd.) dated Jun. 25, 2010 with Exhibits 1-27.
Deposition of Anthony Palmieri, III, Ph.D. dated Jun. 30, 2010 with Exhibits 1-7.
Deposition of Judith D. Goldberg, Sc.D. dated Jul. 2, 2010 with Exhibits 1-7.
Expert Report of Patrick J. Sinko, Ph.D. dated Jul. 9, 2010 with Exhibit 1.
Deposition of James W. Ayers, Ph.D. dated Jul. 9, 2010 with Exhibits 1- 9.
Reply Expert Report of Andrew M. Blumenfeld, M.D. (Alphapharm Pty Ltd.) dated Jul. 21, 2010 with Exhibits 1-3.
Clinical Notes for Patient # 2; Henry Ford Hospital, Department of Neurology, Neurological Evaluation (Exhibit 1 from Deposition of Dr. Nabih Ramadan dated Jun. 24, 2010.
Clinical Notes for Patient #5; Henry Ford Hospital, Department of Neurology, Neurological Evaluation (Exhibit 2 from Deposition of Dr. Nabih Ramadan dated Jun. 24, 2010.
Clinical Notes for Patient #13; Henry Ford Hospital, Emergency Medicine (Exhibit 3 from Deposition of Dr. Nabih Ramadan dated Jun. 24, 2010.
Clinical Notes for Patient #15; Henry Ford Hospital, General Memo (Exhibit 4 from Deposition of Dr. Nabih Ramadan dated Jun. 24, 2010.
English language abstract for JP 2000-336027.
Deposition of Kate Greengrove dated May 20, 2010 with Exhibits 338-370.
Deposition of Donna Gutterman dated May 27, 2010 with Exhibits 371-381.
Fourth Expert Report of Nabih M. Ramadan, M.D., Pursuant to the Court's Memorandum Opinion and Order dated Jun. 8, 2010 with Exhibits A, C, D, E, G, H, I and J.
Supplemental Report of Henry G. Grabowski, Ph.D. dated Jun. 9, 2010 with Attachments A and B.
Supplemental Expert Report of Andrew M. Blumenfeld, M.D. dated Jun. 9, 2010.
Supplemental Expert Report of Chris Gennings, Ph.D. dated Jun. 9, 2010.
Defendants' Amended Invalidity Contentions dated May 17, 2010 with Exhibits A-I.
Defendants' Amended Invalidity Contentions dated Jun. 17, 2010 with Exhibits A-I.
Howard C. Ansel, Remington's Pharmaceutical Sciences, 1721-1725 (Arthur Osol, ed., Mack Publishing Co.) (1980).
Howard C. Ansel & Nicholas G. Popovich, *Pharmaceutical Dosage Forms and Drug Delivery Systems* at 103 (5th ed., Lea & Febiger 1990).
Howard C. Ansel & Nicholas G. Popovich, *Pharmaceutical Dosage Forms and Drug Delivery Systems* at 185 (6th ed., Lea & Febiger 1995).
Brater, D.C., "Clinical Pharmacology of NSAIDs," *J. Clin. Pharmacol.* 28(6):518-523 (1988).
Capone, et al., "Human Pharmacology of Naproxen Sodium," *The Journal of Pharmacology and Experimental Therapeutics* 322(2):453-460 (2007).
Dahl, H., "Naproxen (Naprosyn®). Pharmacokinetics: therapeutical relevance and tolerance profile," *Cephalalgia* Suppl. 4:69-75 (1986).
Ferrari, M., "Migraine," *Lancet* 351:1043-1051 (Apr. 1998).
Ferrari, et al., "Oral sumatriptan: effect of a second dose, and incidence and treatment of headache recurrences," *Cephalalgia* 14:330-338 (1994).

Ferrari, et al., "Subcutaneous GR43175 in the Treatment of Acute Migraine: An International Study," Department of Neurology, University Hospital, Leiden, Holland; Medical Division, Glaxo Group Research Ltd., UK; 348-350.

Fiese, et al., "Preformulation," The Theory and Practice of Industry Pharmacy (Leon Lachman, Ph.D. et al. eds., 1986) at 171.

Geraud, et al., "Comparison of the efficacy of zolmitriptan and sumatriptan: issues in migraine trial design," Cephalalgia 20(1):30-38 (2000).

Geraud, et al., "Migraine Headache Recurrence: Relationship to Clinical, Pharmacological, and Pharmacokinetic Properties of Triptans," Headache 43:376-388 (2003).

Grach, et al., "Can coadministration of oxycodone and morphine produce analgesic synergy in humans? An experimental cold pain study," Br. J. Clin. Pharmacol. 58(3):235-242 (2004).

Headache Classification Committee of the International Headache Society, "Classification and Diagnostic Criteria for Headache Disorders, Cranial and Facial Pain," Cephalalgia 8(Suppl 7): Table of Contents and pp. 9-96 (1988).

Humphrey, et al., "GR43175, a selective agonist for the 5-HT$_1$-like receptor in dog isolated saphenous vein," Br. J. Pharmacol. 94:1123-1132 (1988).

International Headache Society Committee on Clinical Trials in Migraine, "Guidelines for controlled trials in migraine. First edition," Cephalalgia 11(1):1-12 at 5 (1991).

Kaplan, et al., "NSAIDs: Are There Any Differences?" Arch. Fam. Med. 2:1167-1174 (1993).

Kerdelhue, et al., "Acute Acetylsalicylic acid (low dose) potentiation of the dihydroergitamine-induced B-endorphin release: Studies during the luteal phase of the menstrual cycle in healthy women," Cephalalgia 7(Suppl 6):428-429 (1987).

Lacey, et al., "Single dose pharmacokinetics of sumatriptan in healthy volunteers," Eur. J. Clin. Pharmacol. 47:543-548 (1995).

Larkin, et al., "A Randomized, Double-Blind, Comparative Study of the Efficacy of Ketorolac Tromethamine Versus Meperidine in the Treatment of Severe Migraine," Annals of Emergency Medicine 21(8):919-924 (1992).

Luszczki, et al., "Synergistic interaction of gabapentin with tiagabine in the hot-plate test in mice: an isobolographic analysis," Pharmacological Reports 61:459-467 (2009).

Mathew, et al., "Dose Ranging Efficacy and Safety of Subcutaneous Sumatriptan in the Acute Treatment of Migraine," Arch. Neurol. 49(2):1271-1276 (1992).

McCroy, et al., "Oral Sumatriptan for Acute Migraine (Review)," The Cochrane Collaboration, The Cochrane Library 2009, Issue 2: 1-95 (2009).

McCroy, et al., "Oral Sumatriptan for Acute Migraine (Review)," Cochrane Database Systematic Reviews (3) CD002915 (2003).

Moskowitz, M.A., "The Neurobiology of Vascular head Pain," Ann. Neurol. 16(2):157-168 (1984).

Moyer, S., "Pharmacokinetics of naproxen sodium," Cephalalgia Suppl 4:77-80 (1986).

Nicolodi, M., "Sumatriptan and Venoconstriction," Cephalalgia 13:375-377 (1993).

Panconesi, et al., "Amplifying effect of sumatriptan on noradrenaline venoconstriction in migraine," Cephalalgia 13:383-388 (1993).

Peroutka, et al., "Anti-Migraine Drug Interactions with Cloned Human 5-Hydroxytryptamine$_1$, Receptor Subtypes," Headache 33:347-350 (1993).

Pfaffenrath, et al., "Analgesics and NSAIDs in the treatment of the acute migraine attack," Cephalalgia 15:14-20 (1995).

Physicians' Desk Reference, 48$^{th}$ Edition pp. 780-781 (Nov. 1993).

Physicians' Desk Reference, 48$^{th}$ Edition pp. 792-795 (1993).

Physicians' Desk Reference, 48$^{th}$ Edition pp. 2041-2042 (Cafergot®) (1993).

Physicians' Desk Reference, 49$^{th}$ Edition p. 1910 (1994).

Physicians' Desk Reference, 50$^{th}$ Edition pp. 1103-1110 (Nov. 1995).

Physicians' Desk Reference, 50$^{th}$ Edition pp. 2468-2470 (Augmentin) Nov. 1995).

Principles of Pharmacology: Basic Concepts & Clinical Applications, pp. 1659-1660 (Paul L. Munson ed., Chapman & Hall, New York) (1995).

Ramadan, et al., "Migraine and Cluster Headache," In Johnson and Griffin, eds., Current Therapy in Neurological Disease, 4$^{th}$ ed.,, Mosby-year Book, Inc., pp. 79-87 (1990).

Ramadan, et al., "Evidence-Based Guidelines for Migraine Headache and Facial Pain. Setting: Pharmacological Management for Prevention of Migraine," (Apr. 2000) (available at http://www.aan.com/professionals/practice/pdfs/g10090.pdf).

Ramadan, et al., "Migraine prophylactic drugs: proof of efficacy, utilization and cost," Cephalalgia 17(2):73-80 (1997).

Ramadan, N., "Migraine," Encyclopedia of Stress, Second Edition, 733-744 (Fink, G., ed., Oxford) (2007).

Ravin, et al., Preformulation: Remington's Pharmaceutical Sciences (18$^{th}$ ed., 1990) 1435-1450.

Ryan, R., "A Study of Midrin in the Symptomatic Relief of Migraine Headache," St. Louis University School of Medicine.

Sances, et al., "Naproxen Sodium in Menstrual Migraine Prophylaxis: A Double-Blind Placebo Controlled Study," Headache 30:705-709 (1990).

Sargent, et al., "Oral sumatriptan is effective and well tolerated for the acute treatment of migraine: Results of a multicenter study," Neurology 45(Suppl. 7):S10-S14 (Aug. 1995).

Shafer, et al., "Additivity Versus Synergy: A Theoretical Analysis of Implications for Anesthetic Mechanisms," Anesth. Analg. 107(2):507-524 (Aug. 2008).

Silberstein, S.D., "Practice parameter: Evidence-based guidelines for migraine headache (an evidence-based review) Report of the Quality Standards Subcommittee of the American Academy of Neurology," Neurology 55:754-762 (2000).

Silberstein, et al., "Migraine: Diagnosis and Treatment," Wolffs Headache and Other Head Pain, 6$^{th}$ Ed., Delassio and Silberstein, eds., Oxford University Press, New York, 96-170 (1993).

Tallarida, et al., Testing for synergism over a range of fixed ratio drug combinations: replacing the isobologram, Life Sci. 58(2):PL 23-28 (1996).

The Multinational Oral Sumatriptan and Cafergot Comparative Study Group," A Randomized, Double-Blind Comparison of Sumatriptan and Cafergot in the Acute Treatment of Migraine," Eur. Neurol. 31:314-322 (1991).

Tucker, et al., Investigation of the potential of analgesic effects of fentanyl by ketamine in humans: a double-blinded, randomized, placebo controlled, crossover study of experimental pain, BMC Anesthesiology 5:2doi:10.1186/1471-2253-5-2 (2005).

Wilkinson, M., "Treatment of the acute migraine current status," Cephalalgia 3(1):61-67.

Zanchin, et al., "Sumatriptan (50 and 100 mg) in repeated migraine attacks: a patient preference study," J. Headache Pain 1:33-38 (2000).

Ziegler, D.K., "Migraine and Cluster Headache," Current Therapy in Neurological Disease, Johnson RT ed., 3$^{rd}$ ed., B.C. Decker Inc., Philadelphia, Pennsylvania, pp. 70-75 (1993).

Pozen Inc.'s Reply to Defendant Alphapharm Pty Ltd.'s Second Answer and Counterclaims to Pozen Inc.'s Amended Complaint dated Jun. 14, 2010.

Memorandum Opinion and Order dated Jun. 18, 2010.

Report and Recommendations of United States Magistrate Judge dated Jun. 24, 2010.

183 Patent Infringement Report of Robert O. Williams III, Ph.D. (Dr. Reddy's Laboratories, Inc.) dated Apr. 16, 2010 with Exhibits 1-11.

458 Patent Infringement Report Of Andrew M. Blumenfeld, M.D. (Dr. Reddy's Laboratories, Inc.) dated Apr. 16, 2010 with Exhibits 1-25.

499 Patent Infringement Report Of Andrew M. Blumenfeld, M.D. (Dr. Reddy's Laboratories, Inc.) dated Apr. 16, 2010 with Exhibits 1-28.

183 Patent Infringement Report of Robert O. Williams III, Ph.D. (Par Pharmaceutical, Inc.) dated Apr. 16, 2010 with Exhibits 1-15.

458 Patent Infringement Report Of Andrew M. Blumenfeld, M.D. . (Par Pharmaceutical, Inc.) dated Apr. 16, 2010 with Exhibits 1-23.

499 Patent Infringement Report Of Andrew M. Blumenfeld, M.D. . (Par Pharmaceutical, Inc.) dated Apr. 16, 2010 with Exhibits 1-25.

Expert Report of Henry G. Grabowski, Ph.D. dated May 4, 2010 with Appendices A-C and Exhibits 1-11.

Expert Report of Chris Jennings dated May 5, 2010 with Exhibits A-D.

Rebuttal Expert Report of Thomas G. Wiseman, Esq. dated May 5, 2010 with Exhibits A and B.
Rebuttal Expert Report of Robert O. Williams III, Ph.D. with Exhibits 1-3.
Rebuttal Expert Report of Andrew M. Blumenfeld, M.D. dated May 5, 2010 with Exhibits 1-4.
Deposition of Lynda Haberer dated May 14, 2010 with Exhibits 314-337.
183 Reply Patent Infringement Report of Robert O. Williams III, Ph.D. (Dr. Reddy's Laboratories, Inc.) dated May 21, 2010 with Exhibit 1.
183 Reply Patent Infringement Report of Robert O. Williams III, Ph.D. (Par Pharmaceutical, Inc.) dated May 21, 2010 with Exhibit 1.
Reply Expert Report of Andrew M. Blumenfeld, M.D. (Par Pharmaceutical, Inc.) dated May 21, 2010.
Expert Report of Keith B. Leffler, Ph.D. dated May 24, 2010 with Exhibits 1 and 2.
Reply Expert Report of Judith D. Goldberg to the Expert Report of Chris Gennings dated May 24, 2010 with Exhibits 32 and 33.
Reply Expert Report of Anthony Palmieri III, Ph.D. dated May 24, 2010.
Third Expert Report of Nabih M. Ramadan, M.D. dated May 24, 2010.
GSK's Responses to Defendant Par Pharmaceutical, Inc.'s Second Set of Requests for Admission (Nos. 5-36) to GlaxoSmithKline dated May 28, 2010.
Alphapharm Pty Ltd.'s Second Answer to Pozen Inc.'s Amended Complaint and Counterclaims dated May 28, 2010.
Plaintiff Pozen Inc.'s Supplemental Objections and Responses to Defendant Alphapharm Pty Ltd.'s First Set of Interrogatories to Plaintiff (Nos. 1-26) dated May 28, 2010.
Plaintiff Pozen Inc.'s Supplemental Objections and Responses to Defendant Par Pharmaceutical Inc.'s First Set of Interrogatories to Plaintiff (Nos. 1-10) dated May 28, 2010.
Exhibit 326: Summary of MT400-101 and MT400-103 Studies (also included with deposition of Lynda Haberer ).
Exhibit 328: TRX106396 Clinical Study Report (also included with deposition of Lynda Haberer ).
Food and Drug Administration Response letter dated Jun. 8, 2006.
Food and Drug Administration Response letter dated Aug. 1 , 2007.
Study Protocol No. MT400-201 authored and approved Feb. 11, 1998.
Study Protocol No. MT400-202.
MT400-301 Final Clinical Study Report.
MT400-302 Final Clinical Study Report.
MT 400 Tablets; Prototype Approaches.
MT400-103 Final Clinical Study Report.
MT400-101 Final Clinical Study Report.
Henry Ford Hospital Patient Files.
MT100-201 Final Clinical Study Report dated Jan. 30, 2002.
MT400-101 Statistical Analysis Plan authored and approved Sep. 25, 2003.
MT400-103 Statistical Analysis Plan authored and approved Feb. 18, 2004.
Protocol No. MT400-301 approved May 24, 2004.
Protocol No. MT400-301 Statistical Analysis Plan approved Feb. 1, 2005.
Protocol No. MT400-302 approved Jul. 19, 2004.
Protocol No. MT400-302 Statistical Analysis Plan approved Mar. 18, 2005.
Summary of Clinical Pharmacology Studies.
Clinical Study Report, Phase IIIA (Study # 101998) dated Feb. 3, 2006.
Study Report 101999 vol. 3 of 4 dated Mar. 2, 2006.
TRX103632 Protocol dated Jul. 11, 2005.
TRX103632 Clinical Study Report, Phase IIIA dated Jul. 20, 2007.
TRX103635 Protocol dated Jul. 11, 2005.
Par's Opposition to Pozen's Motion to Strike Inequitable Conduct Allegations Directed to the 183 Patent in Par's Second Amended Answer and Counterclaims dated May 21, 2010.
Defendant Par Pharmaceutical, Inc.'s Supplemental Initial Disclosures dated May 21, 2010.
Defendant Par Pharmaceutical, Inc.'s Amended and Supplemented Objections and Responses to Plaintiff Pozen, Inc.'s Second Set of Interrogatories to Defendants (3-12) dated May 21, 2010.
Defendant Par Pharmaceutical, Inc.'s Amended and Supplemented Objections and Responses to Plaintiff Pozen, Inc.'s First Set of Interrogatories (Nos. 1-2) dated May 21, 2010.
Defendants' Reply to Pozen's Opposition to Clarify Mar. 26, 2010 Provisional Claim Construction Order dated May 24, 2010.
Defendant Par Pharmaceutical, Inc.'s Objections and Responses to Plaintiff Pozen, Inc.'s Fourth Set of Interrogatories to Defendants (14-16 (sic)) dated May 28, 2010.
Plaintiff Pozen Inc.'s Supplemental Initial Disclosures dated May 28, 2010.
Plaintiff Pozen Inc.'s Supplemental Responses and Objections to Defendant Par Pharmaceutical, Inc.'s First Set of Requests for Admission (Nos. 1-4) to Pozen dated May 28, 2010.
Plaintiff Pozen Inc.'s Objections and Responses to Defendant Par Pharmaceutical, Inc.'s Third Set of Requests for Admission to Pozen (Nos. 12-81) dated May 28, 2010.
Pozen Inc.'s Reply to Defendant Par Pharmaceutical, Inc.'s Second Amended Answer and Counterclaims to Pozen's Amended Complaint Jun. 1, 2010.
Cady, et al., "Oral Sumatriptan in the Treatment of Recurrent Headache," *Arch. Fam. Med*. 3:766-772 (Sep. 1994).
Fox, et al., "Pharmacokinetic opportunities for combination therapy in migraine," *Neurology* 64(Suppl 2): S21-S25 (May 2005).
Fox, et al., "Consequences of Transforming Measures of Efficacy for Acute Therapies: 5-HT$_{1B/1D}$ Agonists as a Worked Example," *Headache* 44:48-52 (2004).
Freitag, et al., "Efficacy and Tolerability of Coadministration of Rizatriptan and Acetaminophen vs Rizatriptan or Acetaminophen Alone for Acute Migraine Treatment," *Headache* 48:921-930 (2008).
Geraud, et al., "Migraine Headache Recurrence: Relationship to Clinical, Pharmacological, and Pharmacokinetic Properties of Triptans," *Headache* 43:376-388 (2003).
Haberer, et al., "Distinct Pharmacokinetic Profile and Safety of a Fixed-Dose Tablet of Sumatriptan and Naproxen Sodium for the Acute Treatment of Migraine," *Headache* 50:357-373 (2010).
Khoury, et al., "Sumatriptan-naproxen fixed combination for acute treatment of migraine: a critical appraisal," *Drug Design, Development and Therapy* 4:9-17 (2010).
Krymchantowski, et al., "Polytherapy in the preventive and acute treatment of migraine: fundamentals for changing the approach," *Expert Rev. Neurotherapeutics* 6(3):283-289 (2006).
Larsen, et al., "Randomized double-blind comparison of tolfenamic acid and paracetamol in migraine," *Acta. Neurol. Scand*. 81:464-467 (1990).
Lipton, et al., "Stratified Care vs Step Care Strategies for Migraine," JAMA 284(20):2599-2605 (Nov. 2000).
Maggioni, et al., "A study of symptomatic drug use in migraine without aura," *Ital. J. Neurol. Sci*. 16:459-465 (1995).
Ng-Mak, et al., "Acute Migraine Treatment With Oral Triptans and NSAIDs in a Managed Care Population," *Headache* 48:1176-1185 (2008).
Oral Sumartriptan and Asprine plus Meteoclopramide Comparative Study Group, "A Study to Compare Oral Sumatriptan with Oral Aspirin plus Oral Metoclopramide in the Acute Treatment of Migraine," Eur. Neurol. 32:177-184 (1992).
Pfaffenrath, et al., "Analgesics and NSAIDs in the treatment of the acute migraine attack," *Cephalalgia* Suppl. 15:14-20 (1995).
Ramadan, et al., "Evidence-Based Guidelines for Migraine Headache in the Primary Care Setting:Pharmacological Management for Prevention of Migraine," The US Headache Consortium.
Ramadan, et al., "Migraine prophylactic drugs: proof of efficacy, utilization and cost," *Cephalalgia* 17:73-80 (1997).
Tepper, et al.,"Sumatriptan/naproxen sodium combination for the treatment of migraine," Expert *Rev. Neurother*. 8(9):1289-1297 (2008).
Damen et al. "Symptomatic Treatment of Migraine in Children: A Systematic Review of Medication Trials" Pediatrics, 2005 (116), e295-e302.
Hamalainen et al. "Sumatriptan for Migraine Attacks in Children: A Placebo-Controlled Study" Neurology, 1997 (48), 1100-1103.

Haberer et al. "Distinct Pharmacokinetic Profile and Safety of a Fixed-Dose Tablet of Sumatriptan and Naproxen Sodium for the Acute Treatment of Migraine" Headache, 2010 (50), 357-373.

Protocol Amendment 01: TXA107979 (RM2006/00374/01) dated Nov. 18, 2009.

Clinical Pharmacology Study Report: TXA108504 (HM2009/00026/01) dated Jun. 8, 2010.

Protocol: TXA107979 Efficacy Tables dated Jul. 20, 2010.

Protocol: TXA107979 Efficacy Figures dated Jul. 23, 2010.

TXA107979 Results Synopsis dated Jul. 27, 2010.

Trial Transcript: Morning Session on Oct. 12, 2010 (Pozen, Inc. vs Par Pharmaceuticals, Inc.).

Trial Transcript: Afternoon Session on Oct. 12, 2010 (Pozen, Inc. vs Par Pharmaceuticals, Inc.).

Trial Transcript: Morning Session (Sealed Portion-1) on Oct. 13, 2010 (Pozen, Inc. vs Par Pharmaceuticals, Inc.).

Trial Transcript: Morning Session on Oct. 13, 2010 (Pozen, Inc. vs Par Pharmaceuticals, Inc.).

Trial Transcript: Afternoon Session on Oct. 13, 2010 (Pozen, Inc. vs Par Pharmaceuticals, Inc.).

Trial Transcript: Morning Session on Oct. 14, 2010 (Pozen, Inc. vs Par Pharmaceuticals, Inc.).

Trial Transcript: Afternoon Session (Sealed Portion-2) on Oct. 14, 2010 (Pozen, Inc. vs Par Pharmaceuticals, Inc.).

Trial Transcript: Afternoon Session (Sealed Portion-3) on Oct. 14, 2010 (Pozen, Inc. vs Par Pharmaceuticals, Inc.).

Trial Transcript: Afternoon Session on Oct. 14, 2010 (Pozen, Inc. vs Par Pharmaceuticals, Inc.).

Trial Transcript: Session on Oct. 15, 2010 (Pozen, Inc. vs Par Pharmaceuticals, Inc.).

Defendants' List of Trial Exhibits Admitted into Evidence dated Oct. 25, 2010.

Deposition Transcript Excerpts Offered into Evidence by the Parties dated Oct. 25, 2010.

Plaintiff Pozen Inc.'s Trial Exhibits Admitted into Evidence dated Oct. 25, 2010.

Defendant Dr. Reddy's Laboratories, Inc.'s Notice of Submission of Trial Testimony of Judith D. Goldberg dated Nov. 10, 2010 with Exhibits A-M.

Ansel, et al., "Pharmaceutical Dosage Form and Drug Delivery Systems", $5^{th}$ Ed., Lea & Febinger, Philadelphia pp. 99-103 (1990).

Ansel, et al., "Pharmaceutical Dosage Form and Drug Delivery Systems", $6^{th}$ Ed., Lea & Febinger, Philadelphia p. 102 (1990).

Ansel, Howard C., Remington's Pharmaceutical Sciences, Arthur Oslo, ed., Mack Publishing Co. p. 1118 (1990).

Aurora, et al., Comparing Medication Satisfaction Among Probable Migraineurs: Prior Treatment Versus Single Tablet Sumatriptan and Naproxen Sodium (SumaRT/Nap) Versus Placebo, Abstract, American Academy of Neurology Meeting, Seattle, WA P6.004 (Apr. 2009).

Bandelin, Compressed Tablets by Wet Granulation, Pharmaceutical Dosage Forms: Tablets, vol. 1, $2^{nd}$ Ed., Herbert Lieberman, et al. eds., Marcel Dekker, Inc., New York pp. 131 and 279 (1989).

Bangalore, et al., "Of Statistical Significance: "Trends" Toward Significance and Optimism Bias," J. Am. Coll. Cardiol. 48(7):1471 (2006).

Beckman Coulter, Inc., "Simplified Reagent Handling," Therapeutic Drug Monitoring, Acetaminophen (ACTM) Bulletin 9282 tdm 3 (2002).

Benowitz, N. L., "Clinical Pharmacology of Caffeine," Ann. Rev. Med. 41:277-288 (1990).

Brandes, et al., "Sumatriptan + Naproxen: Better than either alone for acute migraine?" The Journal of Family Practice 56(7):536 (Jul. 2007).

Buchanan, et al., "Future pharmacologic targets for acute and preventive treatments of migraine," Expert Rev. Neurotherapeutics 4(3):391-402 (2004).

Burstein, et al., "Therapeutic implications of multimechanism therapy: when to treat?" Neurology 64(Suppl 3):S17-S21 (Jun. 2005).

Chayasirisobhon, S., "Use of Pine Bark Extract and Antioxidant Vitamin Combination Product as Therapy for Migraine in Patients Refractory to Pharmacologic Medication," Headache 46:788-793 (2006).

Cox, D.R., "Interaction," International Statistical Review 52:1-24 (1984).

Damen, et al., "Symptomatic Treatment of Migraine in Children: A Systematic Review of Medication Trials," Pediatrics 116(2):e295-e302 (Aug. 2005).

Davies, O.L., Design and Analysis of Industrial Experiments, $2^{nd}$ ed., Hafner Publishing Co., New York pp. 224-226 and 255 (1963).

Dowson, et al., "Clinical Profile of Botulinum Toxin A in Patients with Chronic Headaches and Cervical Dystonia," Drugs R D 9(3):147-158 (2008).

Eldor, et al., "Ergotamine-Metoclopramide for Migraine: Is it Enough?" Headache 322:466 (Oct. 1992).

Entry in www.Pharmpedia.com entitled "Tablet: Problems in Tablet Manufacturing," http://www.pharmpedia.com/Tablet:Problems_in_tablet_manufacturing#Lamination_.2F_Laminating.

Etherton, et al., "Coffee: Facts and Controversies," Arch. Fam. Med. 2:317-322 (Mar. 1993).

Fitzmaurice, G., "The Meaning and Interpretation of Interaction," Nutrition 16:313-314 (2000).

Fox, A.W., "Onset of Effect of $5\text{-HT}_{1B/1D}$ Agonists: A Model With Pharmacokinetic Validation," Headache 44:142-147 (2004).

Hämäläinen, et al., "Sumatriptan for migraine attacks in children: A randomized placebo-controlled study, Do children with migraine respond to oral sumatriptan differently from adults?" Neurology 48:1100-1103 (1997).

Harrell Jr., F.E., Regression Modeling Strategies with Applications to Linear Models, Logistic Regression, and Survival Analysis, Springer, (New York), Chapter 10 p. 220 (2002).

Hering, et al., "Abrupt outpatient withdrawal of medication in analgesic-abusing migraineurs," The Lancet 337:1442-1443 (Jun. 1991).

Hill, K., "Combination of Sumatriptan and Naproxen for Migraine," JAMA 298(11):1276-1277 (Sep. 2007).

Horisawa, et al., "Influence of Granulating Method on Physical and Mechanical Properties, Compression Behavior, and Compactibility of Lactose and Microcrystalline Cellulose Granules," Drug Development and Industrial Pharmacy 26(6):583-593 (2000).

Houghton, et al., "Effect of sumatriptan, a new selective $5\text{HT}_1$-like agonist, on liquid gastric emptying in man," Aliment. Pharmacol. Ther. 6:685-691 (1992).

Huntjens, et al., "Pharmacokinetic-pharmacodynamic correlations and biomarkers in the development of COX-2 inhibitors," Rheumatology 44:846-859 (2005).

Katic, et al., "Migraine Medication Utilization Patterns among Current Triptan Users," Abstract, American Academy of Neurology Meeting, Seattle, WA [P06.009] (Apr. 29, 2009).

Kawashima, et al., "Improved Static Compression Behaviors and Tablettabilities of Spherically Agglomerated Crystals Produced by the Spherical Crystallization Technique with a Two-Solvent System," Pharmaceutical Research 12(7):1040-1044 (1995).

Kawashima, et al., "Improvements in flowability and compressibility of pharmaceutical crystals for direct tabletting by spherical crystallization with a two-solvent system," Powder Technology 78:151-157 (1994).

Keefer, et al., "Multi-layer Tabletting Q&A," Tablets and Capsules pp. 1-6 (2007).

Lewis, et al., "The Pharmacological Treatment Options for Pediatric Migraine: An Evidence-Based Appraisal," NeuroRx®: The Journal of the American Society for Experimental NeuroTherapeutics 3:181-191 (Apr. 2006).

Lewis, et al., "Practice Parameter: Pharmacological treatment of migraine headache in children and adolescents," Neurology 63:2215-2224 (2004).

Limmroth, et al., "Headache after frequent triptan use," The Lancet 353:1363-1364 (Apr. 1999).

Lipton, et al., "Probable Migrainers' Ability to Function and Productivity: Comparing a Single-Tablet of Sumatriptan and Naproxen Sodium (SumaRT/Nap) to Placebo," Abstract, American Academy of Neurology Meeting, Seattle, WA [P06.003] (Apr. 29, 2009).

Lockwood, A.H., Communication to editor re Silberstein article: Silberstein response, *Neurology* 72:1368-1369 (Apr. 2009).

Mass, et al., "A model-based approach to treatment comparison in acute migraine," *Br. J. Clin. Pharmacol.* 62(5):591-600 (2006).

Migraine: den Teufel mit dem Beelzebub ausgetrieben; Im Blickpundt, Notfall Medizin, (with English translation attached), pp. 410-411 (1994).

Mullins, et al., "Triptans for Migraine Therapy: A Comparison Based on Number Needed to Treat and Doses Needed to Treat," *JMCP* 11(5):394-402 (Jun. 2005).

Pryse-Phillips, et al., "Guidelines for the diagnosis and management of migraine in clinical practice," *Can. Med Assoc. J.* 156(9):1273-1287 (May 1997).

Ramadan, N. M., "Targeting therapy for migraine," *Neurology* 64(Suppl. 2):S5-S8 (May 2005).

Ramadan, et al., "New and future migraine therapy," *Pharmacology & Therapeutics* 112:199-212 (2006).

Ramadan, N. M., "Acute Treatments: Some Blind Alleys," *Current Medical Research and Opinion* 17(Suppl 1):S71-S80 (2001).

Romberg, et al., Pharmacokinetic-Pharmacodynamic Modeling of Morphine-6-glucuronide-induced analgesia in Healthy Volunteers, *Anesthesiology* 100(1):120-133 (Jan. 2004).

Rubenstein, M., Pharmaceutics, The Science of Dosage Form and Design, M. Aulton, ed. Chapter 18 pp. 304-321 (1988).

Rudnic, et al, Remington: The Science and Practice of Pharmacy, 20 ed., Chapter 45, "Oral Solid Dosage Forms," (Daniel Limmer, ed., Lippincott Williams & Wilkins (Baltimore, MD) pp. 858-893 (2000).

Snedecor, et al., Statistical Methods, Seventh Edition, Iowa State University Press, Ames Iowa, pp. 52-53 and 301 (1980).

Silberstein, et al., "Multimechanistic (sumatriptan-naproxen) early interventions for the acute treatment of migraine," *Neurology* 71:114-121 (2008).

Silberstein, et al., "From migraine mechanisms to innovative therapeutic drugs," *Neurology* . 64(2):S1-S3 (May 2005).

Tack, et al., "Actions of the 5-hydroxytrptamine 1 receptor agonist sumatriptan on interdigestive gastrointestinal motility in man," *Gut* 42:36-41 (1998).

Tepper, et al., "Acute Treatment of Migraine," *Neurol Clin* 27:417-427 (2009).

Tfelt-Hansen, et al., "Guidelines for controlled trials of drugs in migraine: second edition," *Cephalalgia* 20(9):765-786 (2000).

The Merck Index, 13th ed. (2001) p. 7588.

Van Der Kuy, et al., "Hydroxocobalamin, a nitric oxide scavenger, in the prophylaxis of migraine: an open, pilot study," *Cephalalgia* 22:513-519 (2002).

Van Der Zwan, et al., "The Compaction and Mechanical Properties of Agglomerated Materials," *Powder Technology* 33:43-54 (1982).

Vécsei, et al., "Dilofenac epolamine is effective in the treatment of acute migraine attacks. A randomized, crossover, double-blind, placebo-controlled, clinical study," *Cephalalgia* 27:29-34 (2007).

Von Seggern, et al., "Rofecoxib in the Prevention of Perimenstrual Migraine: An Open-Label Pilot Trial," *Headache* 44:160-165 (2004).

Waeber, et al., "Migraine as an inflammatory disorder," *Neurology* 64(Suppl 3):S9-S15.

Winner, et al., "Rizatriptan 5 mg for the Acute Treatment of Migraine in Adolescents: A Randomized, Double-Blind, Placebo-Controlled Study," *Headache* 42:49-55 (2002).

Defendants' Notice of Prior Art Under 35 U.S.C. § 282 dated Sep. 1, 2010.

Order Denying Defendant Par Pharmaceutical, Inc.'s Motion to Exclude Testimony of Thomas G. Wiseman dated Oct. 1, 2010.

Joint Final Pre-Trial Order dated Sep. 28, 2010 with Exhibits A-G.

Letter from J.A. Kemp and Co. regarding Opposition of EP0957914, mailed Oct. 25, 2007.

Letter from Gill Jennings & Every regarding Opposition of EP0957914, mailed Sep. 14, 2007.

PDR Entry for Axert Tablets, published Jun. 2005.

RBC Capital Markets, Research Comment on Pozen, Inc. dated Aug. 30, 2005.

HSBC Global Research report on Pozen, Inc. dated Dec. 12, 2005.

"Pozen Inc. and GlaxoSmithKline Report Receipt of Approvable Letter for Investigational Migraine Treatment", Press Release, Jun. 9, 2006.

"FDA Issues Second Approvable Letter for Trexima", Press Release, Aug. 2, 2007.

Cephalalgia, May 1997, vol. 17, Issue 3, Selected abstracts from the 8th Congress of the International Headache Society.

Ferrari et al. Oral Triptans (serotonin 5-HT1B/1D agonists) in Acute Migraine Treatment: A Meta-analysis of 53 Trials, Nov. 2001.

Macor et al. "3-(1,2,5,6-Tetrahydropyrid-4-yl)pyrrolo[3,2-b]pyrid-5-one: A Potent and Selective Serotonin (5-HT1B) Agonist and Rotationally Restricted Phenolic Analogue of 5-Methoxy-3-(1,2,5,6-tetrahydropyrid-4-yl)indole" J. Med. Chem., 1990, 33, 2087-2093.

Letter from J.A. Kemp and Co. regarding Opposition of EP0957914, mailed Sep. 13, 2007.

North, Peter J. "Migraine Therapy—from Serotonin to Sumatriptan" in Medicinal Chemistry: Principles and Practice, Ed. Frank D. King, 1999, pp. 264-277.

EPO Summons to Attend Oral Proceedings of EP0957914 mailed Mar. 5, 2007.

EPO Decision regarding Opposition of EP0957914 mailed Nov. 29, 2007.

Letter from Winston and Strawn regarding ANDA filed by Sun Pharma Global FZE.

* cited by examiner

METHODS OF TREATING HEADACHES USING 5-HT AGONISTS IN COMBINATION WITH LONG-ACTING NSAIDS

CROSS REFERENCE TO RELATED APPLICATIONS

The present application is a continuation-in-part of U.S. Ser. No. 09/559,753, filed Apr. 27, 2000 (now U.S. Pat. No. 6,586,458) which is a continuation-in-part of U.S. Ser. No. 09/151,912, filed Sep. 11, 1998 (now U.S. Pat. No. 6,060,499) and also a continuation-in-part of U.S. Ser. No. 09/252,278, filed Feb. 19, 1999 (now abandoned). The '912 application is a division of U.S. Ser. No. 08/907,826, filed Aug. 14, 1997 (now U.S. Pat. No. 5,872,145) which claims priority to U.S. provisional application 60/024,129, filed on Aug. 16, 1996 (now abandoned).

FIELD OF THE INVENTION

The invention is directed to methods of treating patients for headache by administering compositions containing a 5-HT$1_B$/$1_D$ agonist, preferably sumatriptan, and a long-acting NSAID, preferably naproxen. Other preferred long-acting NSAIDs include cyclooxygenase-2 inhibitors (COX-2 inhibitors).

BACKGROUND OF THE INVENTION 5-hydroxytryptamine (5-HT), also known as serotonin or enteramine, is a vasoactive agent and an endogenous neurotransmitter. It acts on receptors found in the central and peripheral nervous system as well as on blood vessels. Other drugs acting at these receptor sites are known as 5-HT agonists or antagonists. The 5-HT receptors have been divided into several sub-classes, some of which themselves contain subtypes. Examples of subtypes of serotonin receptors are 5-HT1, 5-HT1-like, 5-HT$1_B$, 5-HT$1_D$, 5-HT2, 5-HT3, etc.

Agonists that act preferentially at 5-HT$1_B$ and 5-HT$1_D$ receptors, the triptans, make up a group of therapeutics that may be used for the treatment of migraine headache. A representative member of this group is sumatriptan succinate (distributed under the name Imitrex™ by Glaxo Wellcome, and described in U.S. Pat. No. 4,816,470). Unfortunately, it has been reported that many patients who experience migraine symptom relief within two hours after receiving a 5-HT agonist, experience migraine symptoms again within the next 24 hours. These subsequent headaches are typically termed "rebound," "relapse," "recurrent" or "secondary" headaches.

A variety of analgesics have also been administered to migraine patients. For example, K. M. A. Welch (*New Eng. J. Med.* 329:1476-1483 (1993)) sets forth the following dosages of analgesics as being useful: aspirin, 500-650 mg; acetaminophen, 500 mg; naproxen sodium, 750-825 mg; tolfenamic acid, 200-400 mg; and ibuprofen, 200 mg. However, these agents, when taken alone, are rarely effective in providing complete relief symptoms and, after initial remission, migraine symptoms often return.

The problems that occur with migraine headaches may also be present in other types of headache as well. In all cases, an ideal therapy would reduce or eliminate the symptoms associated with the initial attack and minimize the frequency of later recurrences.

RELATED ART

The following studies provide background information that should aid in understanding the present invention.
1. Plosker, et al., *Drugs* 47:622-655 (1994).
2. Sheftel, et al., *Headache* 34:67-72 (1994).
3. Wilkinson, et al., *Cephalalgia* 15:337-357 (1995).
4. Silberstein, S D, *Curr. Opin. Neurol.* 7:258-263 (1994).
5. Welch, K. M. A., *New Eng. J. Med.* 329:1476-1483 (1993).
6. Kumar, K. L., *J. Gen. Int. Med.* 9:339-348 (1994).

SUMMARY OF THE INVENTION

The present invention is based upon the discovery that co-administration of an agonist that acts preferentially at 5-HT$1_B$ and 5-HT$1_D$ receptor subtypes (abbreviated as "5-HT$1_B$/$1_D$ agonists," i.e., the triptans) together with a long-acting, non-steroidal anti-inflammatory drug (LA-NSAID) represents an improved treatment for a wide variety of headaches. Compared to the administration of either drug alone, the combination produces longer lasting efficacy and a substantial reduction in the frequency of relapse of headaches. As used herein, the term "longer lasting efficacy" means that drugs produce relief from symptoms associated with a headache for a longer period of time.

In its first aspect, the invention is directed to a method of treating a patient for headache by administering a 5-HT$1_B$/$1_D$ agonist together with a long-acting, non-steroidal anti-inflammatory drug (i.e., a drug with a pharmacokinetic half life of at least 4 hours and a duration of action of at least 6 hours). Preferably these two agents are administered simultaneously (e.g. within a minute or two of one another), and, most preferably, together in a single oral dosage form. Oral dosage forms include tablets, capsules, dragees, trochees and other forms that are equivalent to these. The amount of 5-HT$1_B$/$1_D$ agonist and LA-NSAID administered should be sufficient to reduce the frequency of headache relapse in patients or produce longer lasting efficacy compared to the administration of either one of these agents in the absence of the other. This procedure may be used to treat headaches falling into any of a wide variety of classes including: migraine headache; tension-type headache; cluster headache and chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain. (For a description of classes, see Olesen, et al., *The Headaches*, pp. 9-14, Raven Press; see also, "Classification and diagnostic criteria for headache disorders, cranial neuralgias and facial pain," Headache Classification Committee of the International Headache Society, *Cephalalgia* 8(supp. 7):1-96 (1988)).

The invention is also directed to a pharmaceutical composition useful in treating headache patients and which contains, in a single oral dosage form, a 5-HT$1_B$/$1_D$ agonist and a long-acting, non-steroidal, anti-inflammatory drug (LA-NSAID), i.e., an NSAID with a pharmacokinetic half life of at least 4 hours and a duration of action of at least 6 hours. The two therapeutic agents, i.e., 5-HT$1_B$/$1_D$ agonist and LA-NSAID, should be present in amounts such that they are effective, upon co-timely or simultaneous administration of one or more of the single oral dosage forms to produce longer lasting efficacy compared to the administration of said 5-HT$1_B$/$1_D$ agonist in the absence of said LA-NSAID or the administration of said LA-NSAID in the absence of said 5-HT$1_B$/$1_D$ agonist. The oral dosage forms include tablets, capsules, dragees, trochees and other forms that are equivalent to these. The pharmaceutical composition may be included as part of a therapeutic package in which one or more single oral dosage forms are placed in a finished pharmaceutical container. Labeling may be included to provide directions for using the pharmaceutical composition in the treatment of headache, particularly migraine headaches.

The methods and compositions discussed above are also compatible with non-oral dosage forms and non-oral routes of administration. Thus, agents may be administered intranasally, rectally, parenterally, or transdermally. Dosage forms may include tablets (including quick dissolve tablets), trochees, capsules, caplets, dragees, lozenges, parenterals, liquids, powders, and formulations designed for implantation or administration to the surface of the skin. Optionally, these dosage forms may be coordinated or designed for the slow release of therapeutic agents. They can be prepared using methods that are standard in the art and may include additional therapeutic agents, e.g., one or more additional analgesics.

Preferred 5-HT$1_B$/$1_D$ agonists for use in methods and compositions include sumatriptan, eletriptan, rizatriptan, frovatriptan, almotriptan, zolmitriptan, and naratriptan. The most preferred 5-HT$1_B$/$1_D$ agonist is sumatriptan. Among the preferred long-acting NSAIDs for use in compositions and methods are: naproxen, flurbiprofen, oxaprozin, indomethacin, ketorolac, mefenamic acid, piroxicam, etodolac, nabumetone and lornoxicam. Of these, the most preferred is a naproxen or a pharmaceutically acceptable salt of naproxen. This should be administered to patients and present in a unit dose in an amount of greater than 200 mg and preferably between 200 mg and 600 mg. The most preferred oral composition contains sumatriptan in an amount of 5 mg to 100 mg and naproxen in an amount of 200 mg to 600 mg naproxen. Although not essential, it is expected that the sodium salt of naproxen will generally be used. Two specific preferred compositions are: a) a composition containing 85 mg of sumatriptan and 500 mg of naproxen sodium; and b) a composition containing 40 mg of sumatriptan and 400 mg of naproxen sodium.

A second group of preferred long-acting NSAIDs for use with the above compositions and methods are the cyclooxygenase-2 (COX-2) inhibitors. These are defined herein as NSAIDs that inhibit COX-2 to a greater extent than cyclooxygenase-1 (COX-1) and include some of the compounds recited above, especially etodolac and mefenamic acid, both of which have been reported to be highly specific for COX-2 (Feldman, et al., *Ann. Intern Med.* 132:134-143 (2000); Sengupta, *Ind. J. Pharmacol.* 31:322-332 (1999)). Other members include: celecoxib; rofecoxib; meloxicam; JTE-522; L-745,337; NS398; and pharmaceutically acceptable salts thereof. The most preferred of this group is celecoxib in an amount of between 50 and 500 mg. Any of the 5-HT$1_B$/$1_D$ agonists discussed above may be used in combination with the COX-2 inhibitors with sumatriptan being preferred. For example, a method or composition may utilize a dosage of 5 to 100 mg of sumatriptan and 100 to 400 mg celecoxib.

The COX-2 inhibitors, like the other NSAIDs, are especially useful in the treatment of migraine headaches. Thus, the invention includes a method of treating a migraine patient by administering a 5-HT$1_B$/$1_D$ agonist in combination with a COX-2 inhibitor. These agents should be given concomitantly and should be delivered in an amount sufficient to reduce migraine relapse or produce longer lasting efficacy relative to the effect of either agent alone. The invention also includes pharmaceutical compositions in unit dose form which are designed for treating migraine patients and which contain these agents, i.e., a 5-HT$1_B$/$1_D$ agonist and a COX-2 inhibitor. If desired, one or more additional therapeutic agents, e.g., an additional analgesic, may be included. The compositions may be included as part of a therapeutic package in which one or more unit doses are placed in a finished pharmaceutical container. The package may include labeling directing the use of the composition in the treatment of migraine.

DETAILED DESCRIPTION OF THE INVENTION

It has been discovered that a combination therapy of a 5-HT$1_B$/$1_D$ agonist together with a long acting nonsteroidal anti-inflammatory drug (LA-NSAID) substantially reduces or eliminates relapse in a significant portion of headache patients that experience this phenomenon. The combination results in an enhanced therapeutic effect allowing for greater efficacy and/or lower doses than can be obtained with the conventional doses of either individual agent. Naproxen sodium is the most preferred long acting NSAID and sumatriptan is the most preferred 5-HT$1_B$/$1_D$ agonist. The invention will best be understood with reference to the following definitions:

A. "Long acting" in relation to NSAIDs shall mean a pharmacokinetic half-life of at least 4 hours, preferably at least 6 hours and more preferably at least 8-14 hours and a duration of action equal to or exceeding about 6-8 hours. Examples of appropriate NSAIDs are: flurbiprofen with a half-life of about 6 hours; naproxen and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8-9 hours; nabumetone with a half-life of about 22 to 30 hours; mefenamic acid with a half-life of up to about 4 hours; piroxicam with a half-life about of about 4 to 6 hours; and lornoxicam with a half life of about 4 hours. If an analgesic does not naturally have a half life sufficient to be long-acting, it can be made long-acting by the way in which it is formulated. Unless otherwise indicated, the term "long-acting NSAID" shall include NSAIDs (e.g., ibuprofen, or aspirin) specially formulated to be long-acting. Methods for making appropriate long-acting formulations are well known in the art (see e.g., *Remington's Pharmaceutical Sciences,* 16$^{th}$ ed., A. Oslo editor, Easton, Pa. (1980); *Controlled Drug Delivery*, Edith Mathiowitz, John Wiley & Sons (1999), ISBN: 0471148288).

B. "Therapeutically effective amount" as to drug dosage shall mean a dosage that provides the specific pharmacological response for which the drug is administered in a significant number of subjects in need of such treatment. It is emphasized that headaches are not well understood and the etiologies of particular headaches will vary, as does the response to particular drugs. Thus, reference to "specific pharmacological response for which the drug is administered in a significant number of subjects in need of such treatment" is a recognition that a "therapeutically effective amount," administered to a particular subject in a particular instance may not abort the onset of a headache or relieve headache pain, even though such dosage is deemed a "therapeutically effective amount" by those skilled in the art. It is to be further understood that drug dosages are, in particular instances, measured as oral, or parenteral or inhaled dosages or with reference to drug levels as measured in blood.

For 5-HT$1_B$/$1_D$ agonists, NSAIDs and non-NSAID analgesics (particularly with respect to those already on the market) a therapeutically effective amount shall include (but not be limited to) the dosage that has been determined as safe and effective for any indication. Nevertheless, in particular applications, this does not exclude substantially lesser (or greater)

dosages than established minimum (or maximum) dosages for which a particular 5-HT$_{1B}$/1$_D$ agonist or NSAID could be used to effectively treat an episode of headache.

Sumatriptan is presently provided as oral tablets of 25 mg, 50 mg and 100 mg and as a parenteral dosage form containing about 6 mg/ml and about 6 mg/0.5 ml for subcutaneous administration. Oral doses of about 1-300 mg are useful for the present methods and compositions with doses of about 5-100 mg being preferred. Peak serum concentrations of approximately 1-300 ng/ml are produced with doses in these ranges. Subcutaneous injections of about 1 to 8 mg of sumatriptan are useful, with particular reference to about 3 to 6 mg doses. Injections produce peak serum concentrations of approximately 1 to 150 ng/ml. Other dosage forms of sumatriptan include, but are not limited to, suppositories, aerosols for inhalation or intranasal administration, and nose drops, all of which may be used in the practice of this invention.

With respect to NSAIDs, it is expected that the skilled practitioner will adjust dosages on a case by case basis using methods well established in clinical medicine. Nevertheless, the following general guidelines may be of help. Indomethacin is particularly useful when contained in tablets of from about 25 to 75 mg, in suppositories of about 50 mg, and in oral suspensions of about 25 mg/5 ml. A typical daily oral dosage of indomethacin is three 25 mg doses taken at intervals during one day, amounting to 75 mg total. However, daily doses of up to about 150 mg are useful in some subjects. Sustained release dosage forms of indomethacin are also available and provide longer lasting blood levels than conventional tablets. In particular, a 75 mg sustained release dosage form can be used as an alternative to 25 mg three times daily or 75 mg twice daily can be substituted for 50 mg three times daily.

Flurbiprofen is particularly useful when contained in tablets of from about 50 to 100 mg. Daily doses of about 100 to 500 mg, and particularly about 200 to 300 mg total are useful.

Naproxen is particularly useful when contained in tablets of from about 200 to about 600 mg and in oral suspensions of about 125 mg/5 ml.

Oxaprozin has a pharmacokinetic half-life of 42-50 hours and a bioavailability of 95%. It is usefully provided as caplets of 600 mg. Daily doses of 1200 mg have been found to be particularly useful and should not exceed 180 mg or 26 mg/kg. The lowest effective dose should always be used.

Etodolac is usefully provided in capsules of 200 mg and 300 mg or in tablets of 400 mg. Useful doses for acute pain are 200-400 mg every 6-8 hours, not to exceed 1200 mg/day. Patients<60 kg are advised not to exceed doses of 20 mg/kg. Amounts for other uses are also limited to 1200 mg per day, preferably in divided doses, e.g., 2, 3, or 4 times daily.

Ketorolac is usefully provided in tablets of 10 mg and as a sterile parenteral preparation for injection in 15 mg/ml and 30 mg/ml dosage forms. Oral doses of up to 40 mg with particular reference to 10-30 mg per day and parenteral doses up to 120-150 mg per day have been useful in the amelioration of pain.

Nabumetone is usefully provided in tablets of 500 mg and 750 mg. Daily doses of up to 1500-2000 mg/day after an initial dose of 1000 mg are of particular use.

Mefenamic acid is particularly useful when contained in capsules of from about 250 mg. For acute pain such as migraine, an initial dosage of about 100 to 1000 mg and particularly about 500 mg is useful, though other dosages may be required for specific subjects.

Meclofenamate sodium is usefully provided as capsules of 50 mg and 100 mg. Daily doses up to 400 mg are useful, particularly in individual doses of 50-100 mg every 4-6 hours.

Piroxicam is particularly useful when in tablets of from about 10 to 20 mg. It is noted that, as steady state plasma concentrations are not reached until about 7 to 12 days of dosing, prophylactic use of piroxicam is a specific avenue of therapy to establish a plasma concentration of greater than about 5 to 6 µg/ml. In such a situation, coordination and co-timely administration of a 5-HT$_{1B}$/1$_D$ agonist is achieved by the administration of the 5-HT$_{1B}$/1$_D$ agonist approximately at the onset of a migraine attack.

Celecoxib (Celebrex®) is particularly useful when contained in tablets of from about 100 to 200 mg. Recommended dosages are typically 100 mg twice per day or 200 mg once per day. A sub-med amount of celecoxib is less than about 150 mg per day and particularly less than about 100 mg per day, e.g., about 75 mg per day or 50 mg per day (see, Bolten, J., *Rheumatolog. Suppl.*, 51:2-7 (May, 1998)). Celecoxib peak plasma concentrations occur approximately 3 hours after oral dosing. The effective half-life is approximately 11 hours. In one embodiment, coordination and co-timely administration of a 5-HT$_{1B}$/1$_D$ agonist is achieved by the administration of the 5-HT$_{1B}$/1$_D$ agonist approximately at the onset of a migraine.

Rofecoxib (Vioxx®) for oral administration is available in tablets of 12.5, 25 or 50 mg and in an oral suspension containing either 12.5 mg or 25 mg rofecoxib per 5 ml. The recommended initial daily dosage for the management of acute pain is 50 mg. Peak plasma concentrations of rofecoxib typically occur about 2-3 hours after oral administration and the drug has a half life of about 17 hours.

Valdecoxib (Bextra®) for oral administration is available in tablets of 10 or 20 mg. The recommended daily dosage for dysmenorhea is 20 mg or 40 mg. Peak plasma concentrations of valdecoxib typically occur about 2-3 hours after oral administration and the drug has a half life of 8-11 hours.

Lornoxicam for oral administration is available as tablets of 4 mg or 8 mg or as a powder to be reconstituted for injection at 4 mg/ml. Typical dosage schedules include a dose of 4 mg administered 4 times a day or 8 mg administered twice a day. Lornoxicam has a plasma half-life of approximately 4 hours and reaches a peak concentration approximately two hours after administration.

Many scientific articles have suggested that COX-2 specific inhibitors may sometimes offer advantages over nonselective inhibitors. While not being bound by any theory, it is believed that the GI and renal toxicity associated with use of NSAIDs is the result of COX-1 inhibition, stemming from a reduction in the protective prostaglandins that preserve the integrity of the stomach lining and maintain normal renal function. Likewise, anti-inflammatory effects are believed to be largely due to inhibition of COX-2 and the resultant decreases in pro-inflammatory prostaglandins, like thromboxane. Drugs which selectively inhibit the COX-2 isozyme, like mefenamic acid, etodolac, celecoxib, rofecoxib, meloxicam, JTE-522, etorocoxib, valdecoxib and L-745,337, produce analgesia and reduce inflammation without removing the protective prostaglandins in the stomach and kidney.

In certain embodiments, selective inhibition of the COX-2 isozyme may provide a beneficial therapeutic profile in the treatment of headaches, particularly migraine headaches. While the precise etiology of migraine remains unknown, the intense head pain is thought to result from sensitization and neurogenic inflammation at the trigeminal sensory nerve terminals which enervate cerebral blood vessels. NSAIDs have been shown to alleviate migraine headache pain, probably through a combination of their analgesic and anti-inflammatory properties. In the practice of the present invention, selective inhibitors of COX-2 (which have little effect on COX-1)

produce similar effects, based on the preservation of prostacyclin levels, while being better tolerated in terms of potential GI and renal toxicity, and this effect is not negated in combination with 5-HT$_{1B}$/1$_D$ agonists. Additional information on COX-2 inhibitors may be found in the following references:
1. Sharma-S, et al., *Indian J. Exp. Biol.* 35:1025-31 (1997).
2. Lane, *J. Rheumatol* 24 (*Suppl* 49):20-4 (1997).
3. Lipsky, et al., *J. Rheumatol.* 24 (*Suppl* 49):9-14 (1997).
4. Furst, *Semin. Arthritis. Rheum* 26 (6 *Suppl* 1):21-7 (1997). Note particularly the dosage range of meloxicam at about 7.5 mg per day or more, and including 15 mg per day in arthritis pain indications.
5. Donnelly et al., *Aliment-Pharmacol-Ther.* 11(2):227-36 (1997).
6. Griswold, et al., *Med. Res. Rev.* 16(2): 181-206 (1996).

C. "Co-timely" with respect to drug administration means administration of a second drug for headache symptom relief while a first drug is still present in a therapeutically effective amount.

D. "Coordinated" in the practice of the present invention means administration of an NSAID in such a manner that effective plasma levels of the NSAID are present in a subject from about one hour to about 12-24 hours after the onset of migraine or onset of precursor symptoms of a migraine. In some embodiments, this will be about 1 to 12 hours after a 5-HT$_{1B}$/1$_D$ agonist has been administered. The coordination time is clearly related to the route of NSAID administration. For example, intramuscular routes will generally have shorter lead times to peak plasma levels for particular NSAIDs as follows: flurbiprofen peaks in about 1 to 2 hours; naproxen and naproxen sodium peak at about 2 to 4 hours and 1 to 2 hours respectively; oxaprozin peaks at about 3 to 5 hours; etodolac peaks at about 1 to 2 hours; indomethacin peaks at about 1 to 4 hours; ketorolac peaks about one-half to 1 hour; nabumetone peaks at about 2.5 to 4 hours; mefenamic peaks at about 2 to 4 hours; meclofenamate peaks in 0.5-1 hours; and piroxicam peaks at about 3 to 5 hours.

E. "5-HT$_{1B}$/1$_D$ agonist" is to be understood to encompass drugs that act preferentially at 5-HT$_{1B}$ and 5-HT$_{1D}$ receptors. As used herein the term is synonymous with "triptan." In this regard, particular reference is made to sumatriptan succinate and related heterocyclic compounds described in U.S. Pat. No. 4,816,470; eletriptan as described in European Patent Application 379314; Allelix ALX 1323; rizatriptan; frovatriptan; and almotriptan; and naratriptan.

F. "Relapse headaches" variously and interchangeably termed "rebound," "relapse," "recurrent" or "secondary" headaches occur when people experiencing initial symptom relief (or avoidance of migraine in the case of treated precursor symptoms) upon administration of a therapeutic agent, experience a return of headache or other related symptoms within the next 24 hours.

G. "Initial migraine relief" shall be understood to be the reduction or abolition of symptoms from first onset of either a migraine attack or the precursor indicia of a migraine headache such as the aura and visual "scotoma" in about a 24 hour period.

H. "Unit dosage from" shall mean a single drug administration entity. By way of example, a single tablet, capsule, dragee, or trochee, suppository, or syringe combining both a 5-HT$_{1B}$/1$_D$ agonist and an NSAID would be a unit dosage form. Administration of one or more unit dosage forms will result in blood levels of the NSAID required to produce a therapeutic effect within about the first hour after dosing and will still be present at least about 8-12 hours after initial dosing, and in particular instances, for as long as about 24 hours after dosing. Blood levels of the 5-HT$_{1B}$/1$_D$ agonist normally associated with a therapeutic effect will be present within the first hour and should persist in measurable quantities for at least about 4-6 hours.

I. "Quick dissolve" in reference to a tablet or other oral dosage form shall mean that the oral dosage form is at least 95% dissolved within 20 minutes after administration. In determining "quick dissolve," reference is made to standard USP test methodology.

J. "Enhanced therapeutic effect" in the context of the present invention means that the initial relief of migraine symptoms occurs more quickly with a claimed combination of two agents compared to the same doses of each component given alone; or that doses of one or both component(s) are below what would otherwise be a minimum effective dose (a "sub-MED").

While the experienced clinician is able to monitor and adjust dosages for each patient relative to the severity of the headache attack and the presence of side-effects, generally available information on maximum common daily dosages of NSAIDs is useful as a cautionary guideline. Maximum daily dosages in milligrams are as follows: flurbiprofen 300; naproxen 1500, naproxen sodium 1375; oxaprozin 1800; etodolac 1200; indomethacin 150 to 200; ketorolac 120 mg i.m. and 40 oral; nabumetone 2000; mefenamic acid 1000; and piroxicam 20. In particular instances, however, exceeding these "maximum" doses is the therapeutic choice of the medical professional.

The 5-HT$_{1B}$/1$_D$ agonist and NSAID combined compositions of the present invention possess valuable pharmacological properties. They effect long term migraine attack relief with a substantially reduced incidence of relapse headaches. In some instances, they provide initial migraine relief with a reduced incidence of side effects, and/or greater efficacy. This effect can be demonstrated, for example, using the methods employed in the clinical studies reviewed by Plosker and McTavish (*Drugs* 47:622-651 (1999); Wilkinson, et al., *Cephalalgia* 15:337-357 (1995)) and Visser, et al., (*Cephalalgia* 16:264-269 (1996)).

The pharmacologically active compositions of the invention can be produced in accordance with conventional methods of Galenic pharmacy for making medicinal agents for administration to patients, e.g., mammals including humans. The compositions, individually or in combination, are employed in admixture with conventional excipients, i.e., pharmaceutically acceptable organic or inorganic carrier substances suitable for parenteral, enteral (e.g., oral or intranasal) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxymethycellulose, polyvinylpyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents. They can also be combined with other active agents, e.g., vitamins. In some embodiments of the present invention, dosage forms include instructions for the use of such compositions. For parenteral application, particularly suitable are injectable, sterile solutions, preferably oily or aqueous solutions, as well as suspensions, emulsions, or implants, including suppositories. Ampules, vials, and injector cartridges are convenient unit dosages.

Generally, the compositions of this invention are dispensed in unit dosage forms comprising 5-100 mg of sumatriptan or equivalent doses of other 5-HT$1_B$/$1_D$ agonists and 200-600 mg of naproxen sodium or equivalent doses of other NSAIDs in a pharmaceutically acceptable carrier per unit dosage. The actual preferred amounts of active compositions in a specific case will vary according to the specific compositions being utilized, the particular compositions formulated, the mode of application, and the particular route of administration. Dosages for a given subject can be determined using conventional considerations, e.g., by customary comparison of the differential activities of the subject compositions and of a known agent, or by means of an appropriate, conventional pharmacological protocol.

Although many different formulations are compatible with the present invention, the most preferred dosage form is a tablet for oral administration comprising 35-40 mg (most preferably 40 mg) of sodium succinate, and 375-400 mg (most preferably 400 mg) naproxen sodium. When using a triptan and naproxen, substantially all of the triptan should be found in one layer of the tablet and substantially all of the naproxen in a second, separate layer. These two layers should be in a side-by-side arrangement such that the dissolution of the naproxen occurs independently of the dissolution of triptan. This may be achieved by juxtaposing the layers symmetrically along a single planar surface so that essentially all of the triptan-containing layer is on one side of the plane and essentially all of the NSAID-containing layer is on the other side. These layers may come into direct contact with one another or, alternatively, they may be separated by one or more additional layers, e.g., a barrier layer or coating which prevents the therapeutic agents from interacting with one another. In preferred embodiments, the tablets are in a bilayer arrangement and may be surrounded with a film coating. Preferred formulations for each layer of the tablet are provided in Example 4 and appropriate manufacturing methods are provided in Examples 5 and 6.

EXAMPLES

Example 1

Evidence of Synergy with Respect to Relapse and Efficacy

A study was conducted to evaluate the combination of sumatriptan and the long acting NSAID naproxen in migraine patients known to have a high relapse rate, greater than 50% recurrence, when given sumatriptan alone. This was an open-label, randomized out-patient study in which 16 patients treated two successive migraine attacks with either sumatriptan alone (50 mg) or with sumatriptan (50 mg) plus naproxen as the sodium salt (500 mg). Headache pain was assessed by the patients on a 4-point scale (no pain, mild pain, moderate pain, or severe pain). Each patient was treated for two migraine attacks of moderate or severe intensity at baseline and pain scores were recorded every 30 minutes for the first two hours following dosing and at 3, 4, 6, 12 and 24 hours post-dose. "Relapse" was defined to occur in those patients who responded with an adequate reduction in headache pain (moderate or severe at baseline, reduced to no pain or mild pain) at 2 hours after administration and, in whom, over the next 22 hours either: (a) headache pain returned to moderate or severe intensity; or (b) "rescue medication" was required to treat the recurrent headache pain.

In each treatment arm, 13 of the 16 patients achieved adequate pain relief at 2 hours. Two patients in each arm took rescue medication prior to the 2 hour assessment point, and one patient in each arm failed to reach the mild or no pain level. This high rate of response was expected since the selected patients were all known responders to sumatriptan. After treatment with sumatriptan alone, 46% of the responding patients experienced a relapse of headache pain during the study period. When sumatriptan was given in combination with naproxen the relapse rate was substantially reduced, to 23%. Thus, based on these relapse rates, seven of 16 patients (44%) achieved a 24 hour sustained response after taking oral sumatriptan alone, whereas 10 of 16 patients (63%) had a 24 hour sustained response when taking the combination of sumatriptan and naproxen. Thus, the coordinated use of the two agents increased the sustained response rate by over 40%.

This open-label study did not include a treatment arm with naproxen sodium alone, so no direct conclusions could be made regarding the comparative relapse and 24 hour sustained response rates. However, in a second, larger, Phase II study (which compared another experimental compound with a control formulation of naproxen sodium alone) a group of 57 patients were treated for a single migraine attack of moderate or severe intensity with the control formulation containing 500 mg of naproxen sodium. Headache relief at two hours was determined in a manner identical to that described above, but the relapse and sustained response rates were calculated based solely on a return of moderate or severe headache pain (i.e., no "rescue medication" protocol was used as a separate indicator of relapse).

In order to compare the results from the first, 16 patient, study with the second study's treatment arm receiving 500 mg of naproxen sodium as a single agent, the sumatriptan+ naproxen data in the first study were analyzed using the same criteria as the second study (i.e., the relapse and 24 hour sustained response rates were calculated based solely on a return of moderate or severe headache pain). It was found that 40% of the patients receiving sumatriptan alone experienced relapse and 26% of patients had relapse when treated with 500 mg naproxen sodium alone. When sumatriptan and naproxen were given together, none of the 13 responding patients experienced a return of moderate or severe pain.

The results on relapse discussed above were only concerned with patients that initially responded to therapy. Another measure of effectiveness is the "sustained response rate." A sustained responder is a patient that: (a) initially responds to therapy; and (b) does not experience a relapse in twenty-four hours. For example, if results indicated that three people administered a treatment at the onset of a migraine headache did not respond at all, two people responded but had a relapse within twenty-four hours, and five people responded with no relapse, then the sustained response rate would be 50%. (In contrast, the relapse rate, which only considers responders, would be 2 of 7 or 29%.) Using this measure, it was found that sumatriptan alone gave a 56% sustained response rate, and naproxen alone gave a 46% sustained response rate. However, when the two drugs were given together, the sustained response rate was found to increase to 94%.

Based upon these results it was concluded that the treatment of migraine headache using the combination of a long acting NSAID and a 5-HT$1_B$/$1_D$ agonist exhibits a synergistic effect.

Example 2

Evidence for Synergy in Rapid Pain Relief and for Other Migraine Symptoms—Additional Evidence with Respect to Sustained Pain Relief In addition to the data presented above, data was obtained suggesting that triptans and long acting NSAIDs produce a surprising reduction in total, pain relief. In these experiments, a comparison was made between: patients administered triptan alone; patients administered NSAID alone; patients administered a combination of triptan and NSAID ("MT400"); and, in some cases, patients administered a placebo. The results demonstrate, inter alia, that when the combination is used, there is a dramatic increase in the percentage of patients that experience rapid, within two hours, pain relief. The results suggest that, in addition to the synergistic effects relating to relapse, there is also synergy with respect to both the short term and sustained pain response, parameters that are obviously of great importance to patients.

It was found that, at two hours, 65% of patients receiving the combination experienced an improvement from moderate or severe pain at baseline to mild or no pain, compared to 49% receiving the triptan alone, 46% receiving naproxen alone and 27% receiving placebo. Sustained response was evaluated based upon the number of patients that experience an initial pain response without a return of pain for the 24 hours after dosing. The sustained response data are shown in Table 1 below. Analysis of the sustained response data demonstrated that a significantly ($p<0.001$) higher percentage of subjects treated with MT 400 (46%) had a sustained response than subjects treated with either of the individual components (Imitrex, 28.8%; naproxen, 24.7%) or placebo (17%).

TABLE 1

Sustained Pain Response

| Parameter | Treatment Groups | | | |
|---|---|---|---|---|
| | MT 400 (N = 250) | Imitrex (N = 229) | Naproxen (N = 247) | Placebo (N = 241) |
| Sustained Response | 115 (46.0%) | 66 (28.8%) | 61 (24.7%) | 41 (17.0%) |
| P-value vs. placebo | <0.001 | | | |
| p-value vs. Imitrex | <0.001 | | | |
| p-value vs. naproxen | <0.001 | | | |

The results are even more surprising when the effect of placebo is taken into accounted. Therapeutic gain is calculated by subtracting the placebo response from the response rates for active treatment. For pain response, patients receiving the combination experienced a therapeutic gain of 38% over placebo, whereas patients receiving the triptan alone experienced 22% gain and naproxen alone a 19% gain. For sustained response, the results were also dramatic. Patients receiving the combination experienced a therapeutic gain of 29% over placebo, while patients receiving triptan alone experienced a 12% gain and those receiving naproxen alone experienced 8% gain, thus demonstrating a truly synergistic effect of the combination. Again, the combination is statistically significantly superior ($p<0.05$) to individual components in this measure.

The most desirable outcome for the treatment of migraine is that the pain be eliminated quickly and not return. This outcome measure is termed Sustained Pain Free. Responders are defined as patients having a pain score of 0 at 2 hours and nothing more than 0 from 2 to 24 hours post dose without the need for rescue. Therapeutic gain for this measure was 20.2% for MT 400 versus gains of 5.9% and 6.7% for Imitrex and naproxen, respectively. As shown in Table 2 below, 25% of subjects treated with MT 400 were responders compared to less than 12% for naproxen and Imitrex and 5% for placebo. The response differences between MT 400 and all other treatment groups was significant at $p<0.001$.

TABLE 2

Sustained Pain Free

| Parameter | Treatment Groups | | | |
|---|---|---|---|---|
| | MT 400 (N = 250) | Imitrex (N = 229) | Naproxen (N = 247) | Placebo (N = 241) |
| Sustained Response | 63 (25.2%) | 25 (10.9%) | 29 (11.7%) | 12 (5.0%) |
| P-value vs. placebo | <0.001 | | | |
| p-value vs. Imitrex | <0.001 | | | |
| p-value vs. naproxen | <0.001 | | | |

Example 3

Effect of Combination Therapy on Secondary Symptoms of Migraine

As migraine is a pathological complex characterized by unilateral headache, often accompanied by associated symptoms of nausea, photophobia and phonophobia, efficacy against these other parameters is important in evaluating the efficacy of a drug candidate. The surprising benefits of MT 400 are further demonstrated in its impact on these associated symptoms. Analysis of secondary migraine symptom response is presented in Table 3. The percentage of MT 400 treated subjects with nausea at 2 hours was significantly lower than for placebo. The percentage of subjects with photophobia or phonophobia at 2 hours was significantly lower in the group treated with MT 400 than in either of the component groups or placebo. Only the combination provided relief against any or all secondary symptoms versus placebo to a statistically significant extent, and the combination was statistically significantly superior to individual components with respect to photophobia and phonophobia.

TABLE 3

Associated Symptoms of Migraine

| | Treatment Groups | | | |
|---|---|---|---|---|
| | MT 400 (N = 250) | Imitrex (N = 229) | Naproxen (N247) | Placebo (N = 241) |
| Number (%) with nausea | 70 (28%)** | 73 (31.9%) | 77 (31.2%) | 88 (36.5%) |
| Number (%) with photophobia | 97 (38.8%)* | 115 (50.2%) | 142 (57.5%) | 160 (66.4%) |
| Number (%) with phonophobia | 79 (31.6%)* | 102 (44.5%) | 118 (47.8%) | 138 (57.3%) |

*Statistically different from placebo and components ($p < 0.001$)
**Statistically different from placebo ($p = 0.002$)

Example 4

Formulations

As discussed previously, the most preferred dosage form is a tablet in which sumatriptan in the form of its succinate salt and naproxen in the form of its sodium salt are separated into separate layers of a tablet. The sumatriptan should be present in one layer at 35-40 mg and naproxen should be present in the second layer at 375-500 mg. One preferred formulation for the sumatriptan layer is provided in Table 4 and a preferred formulation for naproxen is provided in Table 5.

TABLE 4

Formulation composition for Sumatriptan 40 mg granulation[1]

| Ingredient | mg/Tablet |
|---|---|
| Intra-Granular Ingredients: | |
| Sumatriptan Succinate | 56.00 |
| Lactose Monohydrate, NF | 56.00 |
| Microcrystalline Cellulose, NF | 13.76 |
| Purified Water, USP[2] | QS |
| Extra-Granular Ingredients: | |
| Microcrystalline Cellulose, NF | 13.76 |
| Croscarmellose Sodium, NF | 1.42 |
| Magnesium Stearate, NF | 1.07 |
| Total | 142.01 |

[1]Free base equivalent. Representative formulation shown above; quantities of excipients may be varied by ±10% to improve pharmaceutical processing efficiencies. A suitable binder may be included depending upon manufacturing process and scale.
[2]Purified Water, USP is removed during the drying process.

TABLE 5

Formulation composition for Naproxen Sodium 400 mg granulation[1]

| Ingredient | mg/Tablet |
|---|---|
| Intra-Granular Ingredients: | |
| Naproxen Sodium, USP | 400.00 |
| Microcrystalline Cellulose, NF | 42.36 |
| Povidone, USP | 18.88 |
| Purified Water, USP[2] | QS |
| Extra-Granular Ingredients: | |
| Microcrystalline Cellulose, NF | 42.36 |
| Croscarmellose Sodium, NF | 10.80 |
| Talc, USP | 21.60 |
| Magnesium Stearate, NF | 4.00 |
| Total | 540.00 |

[1]Representative formulation shown above; quantities of excipients may be varied by ±10% to improve pharmaceutical processing efficiencies. Tablet weight may be adjusted for granulation moisture content.
[2]Purified Water, USP is removed during the drying process.

Example 5

Manufacturing of Dosage Form

The manufacture of bilayer tablets is described below and involves the application of standard methods well known in the art of pharmaceutical sciences (Rubinstein, M. H. In *Pharmaceutics: The Science of Dosage Form Design*; Bandelin, In *Pharmaceutical Dosage Forms: Tablets*, Lieberman, et al. eds., Marcel Dekker, Inc., New York, 1989, p. 131-193; and Carstensen, J. T. In *Pharmaceutics of Solids and Solid Dosage Forms*, John Wiley & Sons: New York, 1977). The separate processes for each granulation incorporate high shear granulation, fluid-bed drying, milling, blending, and lubrication. The formulation composition for each separate granulation is provided in Tables 6 and 7. The dose ratios of the components may be varied within the therapeutic ranges.

Manufacturing Steps

1. Separately charge the respective intra-granular ingredients from Tables 6 (sumatriptan succinate) and 7 (naproxen sodium) into suitable high shear mixer/granulators (Niro/Fielder, GP-1 or PMA-65).
2. Dry mix for 5 minutes using a high impeller speed and a high chopper speed setting. Using a spray gun/nozzle, spray purified water, USP, granulating solution, at a controlled rate, while mixing continuously at the same mixing conditions. Continue to mix under the same conditions for one to three minutes or until proper granulation endpoint is reached. Record the final granulating time (solution addition and post-solution addition), amount of solution added, and mixer power consumption readings.
3. Remove the wet granules from the high shear mixer/granulator and place in a drying bowl and dry in a suitable fluid bed dryer (Niro, MP2/3), using the following conditions to achieve a loss on drying of 1-5%:
   a) inlet air temperature: 25-60° C.
   b) outlet air temperature: 35-55° C.
4. Sample the granulation to determine the moisture content.
5. Mill the dried granulation into a hopper or drum using a suitable mill (Quadro Comil, Model 197S) fitted with a suitable screen (0.094R) and operating at 2,500 rpm.
6. Charge the milled granulation and the respective extra-granular ingredients in Tables 6 and 7 into suitable V-blenders (Patterson-Kelly) or tote blenders (Gallay).
7. Blend for 10 minutes or until uniform.
8. Add lubricants, magnesium stearate and/or talc, through a #40 mesh screen and blend for five minutes.
9. Transfer the separate final blends into double-line polyethylene bags.
10. Weigh the respective quantities of each blend using an analytical balance.
11. Manually compress the respective granulations as bilayer tablets using 7/16" standard concave, round shaped tooling and dies using a laboratory tablet press (Carver, Model C). Load the first layer, naproxen sodium blend, into the die first and tamp to remove entrapped air. Load the second layer, sumatriptan succinate blend, on top of the naproxen sodium layer and compress using 2,000 lbs force. Target a bilayer tablet hardness range of 8 to 14 kp.
12. In-process controls to ensure acceptable bilayer dosage form include respective weights of each layer, hardness (8-14 kp), thickness, friability (<1%), and disintegration (<15 minutes).
13. A barrier layer, consisting of 80:20 mixture of anhydrous lactose, NF and microcrystalline cellulose, NF, may be included between the naproxen sodium and sumatriptan succinate layers.

TABLE 6

Formulation Composition for Sumatriptan 35 mg Granulation[1]

| Ingredient | mg/Tablet |
|---|---|
| Intra-Granular Ingredients: | |
| Sumatriptan Succinate | 49.00 |
| Lactose Monohydrate, NF | 49.00 |
| Purified Water, USP[2] | QS |
| Extra-Granular Ingredients: | |
| Anhydrous Lactose, NF | 98.00 |
| Microcrystalline Cellulose, NF | 10.85 |
| Croscarmellose Sodium, NF | 2.10 |
| Magnesium Stearate, NF | 1.05 |
| Total | 210.00 |

[1]Free base equivalent. Representative formulation shown above; quantities of excipients may be varied by ±10% to improve pharmaceutical processing efficiencies.
[2]Purified Water, USP is removed during the drying process.

TABLE 7

Formulation composition for Naproxen Sodium 375 mg granulation[1]

| Ingredient | mg/Tablet |
|---|---|
| Intra-Granular Ingredients: | |
| Naproxen Sodium, USP | 375.00 |
| Microcrystalline Cellulose, NF | 39.71 |
| Povidone, USP | 17.70 |
| Purified Water, USP[2] | QS |
| Extra-Granular Ingredients: | |
| Microcrystalline Cellulose, NF | 39.71 |
| Croscarmellose Sodium, NF | 10.12 |
| Talc, USP | 20.25 |
| Magnesium Stearate, NF | 3.75 |
| Total | 506.24 |

[1]Representative formulation shown above; quantities of excipients may be varied by ±10% to improve pharmaceutical processing efficiencies. Tablet weight may be adjusted for granulation moisture content.
[2]Purified Water, USP is removed during the drying process.

Example 6

Large Scale Manufacturing of Bilayer Tablets

A. Preparation of Granulations

The separate granulations for bilayer tablet dosage forms may be manufactured by various processes depending upon scale and available equipment. The formulations may be easily adapted for a fluid bed granulation process. One suitable method of manufacture is described below.

The intra-granular ingredients described above are separately charged into a fluid bed granulator (Niro, Model MP 2/3) and the materials are fluidized to achieve a uniform distribution of active ingredient. Using a top-spray nozzle, granulating solution, consisting of purified water, USP and povidone, USP, (or other suitable binders) is dispersed at a controlled rate over the fluidized powder bed. Fluid bed granulation is continued until the proper granulation endpoint is reached. After recording the final granulating parameters and amount of solution added, drying is initiated to achieve a loss of 1-5%. The following drying parameters may be used, including an inlet air temperature of 25 to 60° C. and an outlet air temperature of 35 to 55° C. The dried granulation is milled using a Quadro Comil (Model 196) fitted with a suitable screen. The process may be repeated to yield sub-batches that are later combined to provide the desired quantities of each component granulation. Subsequent processing of fluid bed-granulated naproxen sodium and sumatriptan succinate granulations may be carried out as described in subsections B and C below.

B. Pilot-Scale Bilayer Tablet Manufacturing

The formulation and process for making bilayer tablets may be scaled-up for pilot-scale manufacturing (Batch size ~125,000 tablets) as described below.

The respective intra-granular ingredients are separately charged into high shear mixer/granulators (Fielder, PMA-65 or PMA-300) and mixed for 5 minutes using a high impeller speed and a high chopper speed setting. Using a spray nozzle, spray purified water, USP, granulating solution, at a suitable rate while mixing continuously at the same mixing conditions. Continue to mix under the same conditions for 1 to 3 minutes or until proper granulation endpoint is reached. Record the final granulating time (solution addition and post-solution addition), amount of solution added, and mixer power consumption readings. Remove the wet granules from the high shear mixer/granulator and place in a drying bowl and dry in a suitable fluid bed dryer (Glatt, Model GPCG 30), to achieve a loss on drying of 1-5%. The following drying parameters may be used, including an inlet air temperature of 25 to 60° C. and an outlet air temperature of 35 to 55° C. The dried granulation is milled using a Quadro Comil (Model 196) fitted with a suitable screen. The process may be repeated to yield sub-batches that are later combined to provide the desired quantities of each component granulation.

The milled granulations are transferred to suitable V-blenders (Patterson-Kelly, 2 or 5 cu. ft.) and mixed for approximately ten minutes with the respective extra-granular ingredients. Pre-sifted lubricants are added and blended for five minutes. Transfer the separate final blends into the hopper(s) for a 35-station, rotary bilayer tablet press (Manesty, Model BB-4). Compress the respective granulations as bilayer tablets using oval-shaped, concave tooling. The naproxen sodium layer is loaded into the die cavity first, and minimal compression force (~500 lbs) is applied to remove entrapped air and form a loose compact. Once acceptable tablet weights are obtained for the naproxen sodium layer, the second layer, consisting of sumatriptan succinate granulation, is loaded into the die cavity. Sufficient compression force (~3,800 lbs) is then applied to yield acceptable bilayer tablets with desired mechanical properties. A tablet hardness of 14 to 18 kp and friability of less than 1% are targeted. In-process controls to ensure acceptable bilayer dosage form include respective weights of each layer, hardness, thickness, friability, and disintegration.

The core bilayer tablets are film-coated in a perforated pan-coater (36" Accela-Cota), using a pre-mixed hydroxypropyl methylcellulose (HPMC) polymer-based dispersion with colorants (Opadry®, Colorcon, Inc.). A 12% w/w aqueous coating suspension is typically prepared. The tablets are coated using two spray guns with an inlet temperature of ~60° C. and an outlet temperature of ~40° C. The pan speed may range from 6 to 12 rpm. The finished tablets are stored in double-lined polyethylene bags prior to packaging.

C. Commercial-Scale Bilayer Tablet Manufacturing

The formulation and process may also be successfully scaled-up for commercial-scale manufacturing (Batch size ~1,250,000 tablets). The respective intra-granular ingredients are separately charged into high shear mixer/granulators (Fielder, PMA 300 or PMA-1200). Dry mix for 5 minutes using a high impeller speed and a high chopper speed setting. Using a spray nozzle, spray purified water, USP, granulating solution, at a suitable rate while mixing continuously at the same mixing conditions. Continue to mix under the same conditions for 1 to 3 minutes or until proper granulation endpoint is reached. Record the final granulating time (solution addition and post-solution addition), amount of solution added, and mixer power consumption readings. Remove the wet granules from the high shear mixer/granulator and place in a drying bowl and dry in a suitable fluid bed dryer (Niro Aeromatic, Model T9), to achieve a loss on drying of 1-5%. The following drying parameters may be used, including an inlet air temperature of 25 to 60° C. and an outlet air temperature of 35 to 55° C. The dried granulation is milled using a Quadro Comil (Model 199) fitted with a suitable screen. The process may be repeated to yield sub-batches that are later combined to provide the desired quantities of each component granulation.

The milled granulations are transferred to suitable bin blenders (Bohle Bin Blender) and mixed for approximately ten minutes with the respective extra-granular ingredients, described elsewhere. Pre-sifted lubricants are added and blended for five minutes. Transfer the separate final blends into the hopper(s) for a 51-station, rotary bilayer tablet press (Elizabeth Hata, Model HT-HX51). Compress the respective granulations as bilayer tablets using appropriately shaped tooling. The naproxen sodium layer is loaded into the die cavity first, and minimal compression force (~500 lbs) is applied to remove entrapped air and form a loose compact. Once acceptable tablet weights are obtained for the naproxen sodium layer, the second layer, consisting of sumatriptan succinate granulation, is loaded into the die cavity. Sufficient compression force (~3,800 lbs) is then applied to yield acceptable bilayer tablets with desired mechanical properties. The rotary tablet press speed is approximately 40 rpm. A tablet hardness of 16 to 18 kp and friability of less than 1% are targeted. In-process controls to ensure acceptable bilayer dosage form include respective weights of each layer, hardness, thickness, friability, and disintegration.

The core bilayer tablets are film-coated in a perforated pan-coater (48" Accela-Cota), using a pre-mixed hydroxypropyl methylcellulose (HPMC) polymer-based dispersion with colorants (Opadry®, Colorcon, Inc.). The batch is subdivided to yield suitable pan loading. A 12% w/w aqueous suspension is typically prepared for coating. The tablets are coated using three spray guns with an inlet temperature of ~60° C. and an outlet temperature of ~40° C. The pan speed may range from 4 to 8 rpm. The finished tablets are stored in double-lined polyethylene bags prior to packaging.

Example 7

First Treatment Example

An adult female migraineur complains of a migraine attack consisting of typical migraine headache, nausea and sensitivity to light and sound. She is dosed with a single oral tablet containing sumatriptan 40 mg and naproxen sodium 400 mg. Her symptoms start to diminish within one hour and by three hours she is completely symptom free. No relapse over the next 48 hours is reported.

Example 8

Second Treatment Example

An adult female migraineur complains of a migraine attack consisting of typical migraine headache, nausea and sensitivity to light and sound. She is dosed with a single oral tablet containing 12.5 mg sumatriptan and 550 mg naproxen sodium. Her symptoms start to diminish within one hour. By three hours she is completely symptom free and has no relapse over the next 48 hours.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A pharmaceutical composition useful in treating migraine headache which comprises in a unit dosage form:
    (a) naproxen; and
    (b) sumatriptan;
    wherein the respective amounts of sumatriptan and naproxen in said pharmaceutical composition are effective upon simultaneous administration of one or more unit dosage forms, to produce longer lasting efficacy compared to the administration of sumatriptan in the absence of naproxen or the administration of naproxen in the absence of sumatriptan; and
    wherein the sumatriptan is present at about 85 mg and the naproxen is present at about 500 mg.

2. A pharmaceutical composition useful in treating migraine headache which comprises in a unit dosage form:
    (a) naproxen sodium; and
    (b) sumatriptan;
    wherein the respective amounts of sumatriptan and naproxen in said pharmaceutical composition are effective upon simultaneous administration of one or more unit dosage forms, to produce longer lasting efficacy compared to the administration of sumatriptan in the absence of naproxen or the administration of naproxen in the absence of sumatriptan; and wherein sumatriptan is present at about 85 mg and naproxen sodium is present at about 500 mg.

3. A pharmaceutical composition useful in treating migraine headache which comprises in a unit dosage form:
    (a) naproxen sodium; and
    (b) sumatriptan;
    wherein the respective amounts of sumatriptan and naproxen in said pharmaceutical composition are effective upon simultaneous administration of one or more unit dosage forms, to produce longer lasting efficacy compared to the administration of sumatriptan in the absence of naproxen or the administration of naproxen in the absence of sumatriptan; and wherein sumatriptan is present at about 50 mg and naproxen sodium is present at about 500 mg.

4. A method of treating a patient for a migraine headache, comprising simultaneously administering to said patient:
    (a) sumatriptan; and
    (b) naproxen;
    wherein:
    sumatriptan and naproxen are administered to said patient orally after the onset of migraine symptoms; and
    the amount of sumatriptan and naproxen administered to said patient are sufficient to produce longer lasting efficacy compared to the administration of sumatriptan in the absence of naproxen or the administration of naproxen in the absence of sumatriptan; and wherein sumatriptan is administered at an amount of about 50 mg and naproxen is administered at an amount of about 500 mg.

5. A method of treating a patient for a migraine headache, comprising simultaneously administering to said patient:
    (a) sumatriptan; and
    (b) naproxen;
    wherein:
    sumatriptan and naproxen are administered to said patient orally after the onset of migraine symptoms; and
    the amount of sumatriptan and naproxen administered to said patient are sufficient to produce longer lasting efficacy compared to the administration of sumatriptan in the absence of naproxen or the administration of naproxen in the absence of sumatriptan; and wherein sumatriptan is administered at an amount of about 100 mg and naproxen is administered at an amount of about 500 mg.

6. A method of treating a patient for a migraine headache, comprising simultaneously administering to said patient:
    (a) sumatriptan; and
    (b) naproxen sodium;
    wherein:
    sumatriptan and naproxen sodium are administered to said patient orally after the onset of migraine symptoms; and the amount of sumatriptan and naproxen sodium administered to said patient are sufficient to produce longer lasting efficacy compared to the administration of sumatriptan in the absence of naproxen sodium or the administration of naproxen sodium in the absence of sumatriptan; and wherein sumatriptan is administered at an amount of about 85 mg and naproxen sodium is administered at an amount of about 500 mg.

* * * * *